United States Patent
Gratzer

(10) Patent No.: US 9,566,369 B2
(45) Date of Patent: Feb. 14, 2017

(54) METHODS FOR TISSUE DECELLULARIZATION

(75) Inventor: Paul F. Gratzer, Upper Tantallon (CA)

(73) Assignee: DECELL TECHNOLOGIES INC., Halifax, NS (CA)

( * ) Notice: Subject to any disclaimer, the term of this patent is extended or adjusted under 35 U.S.C. 154(b) by 599 days.

(21) Appl. No.: 13/580,367

(22) PCT Filed: Feb. 25, 2011

(86) PCT No.: PCT/IB2011/001538
§ 371 (c)(1),
(2), (4) Date: Oct. 9, 2012

(87) PCT Pub. No.: WO2011/132089
PCT Pub. Date: Oct. 27, 2011

(65) Prior Publication Data
US 2013/0028981 A1    Jan. 31, 2013

Related U.S. Application Data

(60) Provisional application No. 61/308,872, filed on Feb. 26, 2010.

(51) Int. Cl.
*A61K 35/36*        (2015.01)
*A61K 35/32*        (2015.01)
(Continued)

(52) U.S. Cl.
CPC ............ *A61L 27/60* (2013.01); *A61L 27/3641* (2013.01); *A61L 27/3683* (2013.01); *A61L 2430/40* (2013.01)

(58) Field of Classification Search
None
See application file for complete search history.

(56) References Cited

U.S. PATENT DOCUMENTS 4,801,299 A    1/1989    Brendel et al.
5,116,615 A    5/1992    Gokcen et al.
(Continued)

FOREIGN PATENT DOCUMENTS

CA    2 286 655 A1    10/1998
CA    2 396 698 A1    8/2001
(Continued)

OTHER PUBLICATIONS

Rosenberg et al., Long-Term Histologic Effects of the CO2 Laser, Plastic and Reconstructive Surgery, Dec. 1999, vol. 104, No. 7, pp. 2239-2244.*

(Continued)

*Primary Examiner* — Karen Cochrane Carlson
*Assistant Examiner* — Jennifer M. H. Tichy
(74) *Attorney, Agent, or Firm* — BCF LLP

(57) ABSTRACT

A method for producing sterile, decellurized bioprosthetic tissue comprising: (a) contacting a human tissue with a hypotonic solution to produce a lysed tissue, (b) contacting the lysed tissue with a first surfactant to produce a surfactant-treated tissue, (c) contacting the surfactant-treated tissue with a nuclease enzyme solution to produce an enzyme-treated tissue, (d) contacting the enzyme-treated tissue with a cleaning solution comprising a second surfactant, a chaotropic agent or a mixture thereof to produce a decellurized tissue and (e) contacting the decellurized tissue with a bioburden reducing agent to produce the final bioprosthetic tissue. Kits to be used in conjunction with said method, as well as, the bioprosthetic tissue produced via said method are also provided.

16 Claims, 13 Drawing Sheets

(51) Int. Cl.
A61K 35/34 (2015.01)
A61L 27/60 (2006.01)
A61L 27/36 (2006.01)

(56) References Cited

U.S. PATENT DOCUMENTS

| | | | |
|---|---|---|---|
| 5,336,616 | A | 8/1994 | Livesey et al. |
| 5,460,962 | A | 10/1995 | Kemp |
| 6,613,278 | B1 | 9/2003 | Mills et al. |
| 6,652,818 | B1 | 11/2003 | Mills et al. |
| 6,734,018 | B2 | 5/2004 | Wolfinbarger, Jr. et al. |
| 6,743,574 | B1 | 6/2004 | Wolfinbarger, Jr. et al. |
| 7,067,298 | B2 | 6/2006 | Latham et al. |
| 7,118,901 | B2 | 10/2006 | Suppmann et al. |
| 7,318,998 | B2 | 1/2008 | Goldstein et al. |
| 7,354,749 | B2 | 4/2008 | Fisher et al. |
| 7,402,319 | B2 | 7/2008 | Schmidt et al. |
| 7,628,996 | B2 | 12/2009 | Haspel et al. |
| 7,723,108 | B2 | 5/2010 | Truncale et al. |
| 7,763,081 | B2 | 7/2010 | Olerenshaw et al. |
| 2004/0076657 | A1 | 4/2004 | Wolfinbarger, Jr. et al. |
| 2004/0115172 | A1 | 6/2004 | Bianchi et al. |
| 2005/0013870 | A1* | 1/2005 | Freyman ............ A61L 27/3633 424/520 |
| 2005/0096742 | A1 | 5/2005 | Mills et al. |
| 2005/0256588 | A1 | 11/2005 | Sawa et al. |
| 2007/0123700 | A1 | 5/2007 | Ueda et al. |
| 2008/0188939 | A1 | 8/2008 | DePaula et al. |
| 2008/0306610 | A1 | 12/2008 | Wang et al. |
| 2009/0186333 | A1 | 7/2009 | Mills et al. |
| 2010/0112543 | A1 | 5/2010 | Ngo et al. |

FOREIGN PATENT DOCUMENTS

| | | |
|---|---|---|
| GB | 2 443 938 A | 5/2008 |
| WO | WO 2006/101885 A2 | 9/2006 |
| WO | WO 2008/154623 A2 | 12/2008 |
| WO | WO 2008/154628 A2 | 12/2008 |

OTHER PUBLICATIONS

Melrose et al., Spatial and Temporal Localization of Transforming Growth Factor-β, Fibroblast Growth Factor-2, and Osteonectin, and Identification of Cells Expressing α-Smooth Muscle Actin in the Injured Anulus Fibrosus, Spine, (2002), vol. 27, No. 16, pp. 1756-1764.*
Lee et al., A multi-sample denaturation temperature tester for collagenous biomaterials, Med. Eng. Phys., (1995), vol. 17, No. 2, pp. 115-121.*
Ulthera, White Paper, the Effect of Heat on Collagen and Neocollagenesis, document created Jan. 7, 2013, Available online at: www.ultherapy.com/uploads/document/professional/Effects%20of%20Temperature%20on%20Collagen%20White%20Paper%20-%201001889A.pdf.*
Pereira et al., Review Paper: Burn Coverage Technologies: Current Concepts and Future Directions, Journal of Biomaterials Applications, vol. 22, Sep. 2007, pp. 101-121.*
Oxford Dictionaries, Substantially, Accessed Nov. 13, 2015, Online at: www. oxforddictionaries.com/us/definition/american_english/substantially.*
American Association of Tissue Banks, "13th Edition of AATB Standards for Tissue Banking," Jan. 16, 2012, pp. 1-32, can be retrieved at <URL:http://www.aatb.org/Standards-Updates-for-the-12th-Edition>.
American Association of Tissue Banks, "Current Good Tissue Practice," AATB Guidance Document, No. 3, Jun. 27, 2006, 43 pages.
Azar, F.M., "Tissue Processing: Role of Secondary Sterilization Techniques," Clin. Sports Med., vol. 28, pp. 191-201, 2009.
Cserháti, T., et al., "Biological activity and environmental impact of anionic surfactants," Environment International, vol. 28, No. 5, pp. 337-348, Nov. 2002.
Dyck, C.R., et al., "Decellularization in Tissue Engineering—Principles and Applications," New Research on Biomaterials, D.R. Bloomington (ed.), Nova Science Publishers Inc., Hauppauge, NY, USA, Chapter 11, pp. 281-320, 2008.
Dyck, C.R., et al., "Use of Bone Marrow Stromal Cells to Repopulate Decellularized Anterior Cruciate Ligaments," Proceedings of the 25th Canadian Biomaterials Society, May 26-28, 2006, University of Calgary, Calgary, Alberta, Canada, Abstract 2, 3 Pages.
Dyck, C.R., et al., "Validation of a Decellularized Bone-ACL-Bone Rat Model for ACL Allograft Regeneration Studies," 55th Canadian Chemical Engineering Conference, Toronto, Ontario, Canada, Oct. 16-19, 2005, 1 Page.
Gratzer, P.F., et al., "Matrix Alteration and Not Residual Sodium Dodecyl Sulfate Cytotoxicity Affects the Cellular Repopulation of a Decellularized Matrix," Tissue Engineering, vol. 12, No. 10, pp. 2975-2983, 2006.
Harrison R.D., et al., "Effect of extraction protocols and epidermal growth factor on the cellular repopulation of decellularized anterior cruciate ligament allografts," Journal of Biomedical Materials Research, vol. 75, No. 4, pp. 841-854, Dec. 2005.
Hodde, J., et al., "Virus Safety of a Porcine-Derived Medical Device: Evaluation of a Viral Inactivation Method," Biotechnol. Bioeng., vol. 79, No. 2, pp. 211-216, Jul. 2002.
Horowitz, B., et al., "Solvent/Detergent-Treated Plasma: A Virus-Inactivated Substitute for Fresh Frozen Plasma," Blood, vol. 79, No. 3, pp. 826-831, Feb. 1992.
Horowitz, B., et al., "Viral safety of solvent-detergent treated blood products," Dev. Boil. Stand., vol. 81, pp. 147-161, 1993.
Kearney, J.N., "Guidelines on processing and clinical use of skin allografts," Clinics in Dermatology, vol. 23, pp. 357-364, 2005.
Kitagawa, T., et al., "Cellular biology of cryopreserved allograft valves," J. Med. Invest., vol. 48, Nos. 3-4, pp. 123-132, Aug. 2001.
Lee, J.M., et al., "A multi-sample denaturation temperature tester for collagenous biomaterials," Med. Eng. Phys., vol. 17, No. 2, pp. 115-121, 1995.
Leyh, R.G., et al., "Acellularized porcine heart valve scaffolds for heart valve tissue engineering and the risk of cross-species transmission of porcine endogenous retrovirus," J. Thorac. Cardiovasc. Surg., vol. 126, No. 4, pp. 1000-1004, Oct. 2003.
Liao, J., et al., "Effects of Decellularization on the Mechanical and Structural Properties of the Porcine Aortic Valve Leaflet," Biomaterials, vol. 29, No. 8, pp. 1065-1074, Mar. 2008.
Lüscher-Mattli, M., "Polyanions—a lost chance in the fight against HIV and other virus diseases?," Antiviral Chemistry & Chemotherapy, vol. 11, No. 4, pp. 249-259, Jul. 2000.
MacLean, S.B.A., et al., "Comparison of Seeding Methods Used in the Repopulation of Decellularized Porcine Anterior Cruciate Ligament Tissue," Proceedings of the 25th Canadian Biomaterials Society, May 26-28, 2006, University of Calgary, Calgary, Alberta, Canada, Abstract 62, 3 Pages.
MacLean, S.B.A., et al., "Effect of basic fibroblast growth factor on the cellular repopulation of decellularized anterior cruciate ligament allografts," Journal of Tissue Engineering and Regenerative Medicine, vol. 5, No. 3, pp. 201-209, Mar. 2011.
MacLean, S.B.A., et al., "Repopulation of decellularized porcine anterior cruciate ligaments with porcine ACL fibroblasts: A study into the effects of seeding methodology and the use of basic fibroblast growth factor (bFGF)," Regenerate: World Congress on Tissue Engineering and Regenerative Medicine, Apr. 25-27, 2006, Pittsburgh, PA, USA, 1 Page.
MacLean, S.B.A., et al., "The In vitro Application of Basic Fibroblast Growth Factor (bFGF) for Repopulation of the Decellularized Porcine Anterior Cruciate Ligament (ACL)," 55th Canadian Chemical Engineering Conference, Toronto, Ontario, Canada, Oct. 16-19, 2005, 1 Page (Abstract Only).
Patent Cooperation Treaty, International Search Report and Written Opinion, International Patent Application No. PCT/IB2011/001538, Dec. 22, 2011, 12 Pages.
Pianigiani E., et al., "Processing efficacy in relation to microbial contamination of skin allografts from 723 donors," Burns, vol. 36, No. 3, pp. 347-351, May 2010.

(56) References Cited

OTHER PUBLICATIONS

Simon, P., et al., "Early failure of the tissue engineered porcine heart valve SYNERGRAFT™ in pediatric patients," European Journal of Cardio-thoracic Surgery, vol. 23, No. 6, pp. 1002-1006, Jun. 2003.
Stewart, C.M., et al., "Sensitivity of spores of *Bacillus subtilis* and *Clostridium sporogenes* PA 3679 to combinations of high hydrostatic pressure and other processing parameters," Innovative Food Science & Emerging Technologies, vol. 1, Issue 1, pp. 49-56, Mar. 2000.
Walles, T., et al., "In vivo model for cross-species porcine endogenous retrovirus transmission using tissue engineered pulmonary arteries," European Journal of Cardio-thoracic Surgery, vol. 24, No. 3, pp. 358-363, Sep. 2003.
Williams, C., et al., "Altered structural and mechanical properties in decellularized rabbit carotid arteries," Acta Biomater., vol. 5, No. 4, pp. 993-1005, May 2009.
Wilson, G.J., et al., "Acellular Matrix: A Biomaterials Approach for Coronary Artery Bypass and Heart Valve Replacement," Ann. Thorac. Surg., vol. 60, Suppl. 2, pp. S353-S358, Aug. 1995.
Woods, T., et al., "Effectiveness of three extraction techniques in the development of a decellularized bone-anterior cruciate ligament-bone graft," Biomaterials, vol. 26, No. 35, pp. 7339-7349, Dec. 2005.
Woods, T., M Sc Thesis, Dalhousie University, Halifax, NS, Canada, 2002.

\* cited by examiner

METHODS FOR TISSUE DECELLULARIZATION

CROSS REFERENCE TO RELATED APPLICATIONS

This application claims the benefit of PCT Application No. PCT/IB2011/001538, filed Feb. 25, 2011, which claims the benefit of U.S. Provisional Application No. 61/308,872, filed Feb. 26, 2010, the entire disclosure of which is hereby incorporated by reference in its entirety for all purposes.

FIELD

The disclosure relates generally to the field of bioengineering and in particular to methods for producing decellularized, sterilized, and bioprosthetic tissues.

BACKGROUND

Tissue and organ transplantation is a rapidly growing therapeutic field as a result of improvements in surgical procedures, advancements in immunosuppressive drugs and increased knowledge of graft/host interaction. There are numerous investigations underway directed toward the engineering of improved transplantable tissue grafts, however, it is generally believed in the industry that ideal implants have yet to be produced.

The use of decellularized tissue scaffolds have been explored as a possibility for tissue engineering, however, the existing approaches have proven inadequate. References of interest include U.S. Pat. No. 6,743,574; U.S. Pat. No. 5,336,616; Gratzer et al., Tissue Engineering, 12(10):2975-2983 (2006); Woods et al., Biomaterials, 26:7339-7349 (2005); Williams et al., Acta Biomaterialia, 5:993-1005 (2009); Liao et al., Biomaterials, 29:1065-1074 (2008); Wilson et al., Ann Thorac Surg, 60:S353-S358 (1995); PCT App. Pub. No. WO2006/101885; U.S. Pat. No. 7,318,998; Kitagawa et al., J Med Invest, 48(3-4):123-132 (2001); Kearney, Clin Dermatol, 23:357-364 (2005); Azar, Clin Sport Med, 28:191-201 (2009); and Simon et al., Eur J Cardiothorac Surg, 23:1002-1006 (2003)).

Despite major advancements in the field of biomedical engineering, modern tissue transplantation remains associated with complications including inflammation, degradation, scarring, contracture, calcification (hardening), occlusion, and/or rejection. Moreover, existing technologies for producing decellularized tissue scaffolds have failed to sufficiently reduce the number of cells in the tissue to an adequate level. Therefore, there is a need in the art for methods of producing tissues that avoid or reduce the above-described drawbacks and thus have greater short- and long-term usability. There is also a further need in the art for methods of producing sterile, decellularized tissues.

SUMMARY

Disclosed herein is a method for producing a human bioprosthetic tissue comprising: contacting a human tissue with a hypotonic solution to produce a lysed tissue; contacting the lysed tissue with a first surfactant solution to produce a surfactant-treated tissue; contacting the surfactant-treated tissue with a nuclease enzyme solution to produce an enzyme-treated tissue; contacting the enzyme-treated tissue with a cleaning solution comprising a second surfactant, a chaotropic agent, or a mixture thereof, to produce a decellularized tissue; and contacting the decellularized tissue with a bioburden reducing agent solution to produce the human bioprosthetic tissue. In some embodiments, the method further comprises contacting one or more of the tissues with a physiologically isotonic solution.

In some embodiments, the human tissue is human skin tissue, wherein the hypotonic solution comprises 10 mM Tris buffer, wherein the first surfactant solution comprises 1% (v/v) Triton X-100® (octyl phenoxy polyethoxyethanol), wherein the nuclease enzyme solution comprises RNase and DNase, wherein the cleaning solution comprises 1% (v/v) tri-n-butyl phosphate (TnBP), wherein the bioburden reducing agent solution comprises 1% (v/v) Peracetic Acid, wherein each step of the method is performed separately from the other steps of the method, and wherein each step of the method is immediately followed by a rinsing step prior to the start of the next step of the method. In some embodiments, the method further comprises sonicating one or more of the tissues.

In some embodiments, one or more of the solutions further comprises a protease inhibitor. In some embodiments, the protease inhibitor is a serine protease inhibitor, a metalloprotease inhibitor, or a combination thereof. In some embodiments, the protease inhibitor is ethylenediaminetetraacetic acid (EDTA). In some embodiments, the protease inhibitor is phenylmethanesulfonyl fluoride.

In some embodiments, one or more of the solutions further comprises a bioburden reducing agent. In some embodiments, the bioburden reducing agent comprises penicillin, streptomycin, peracetic acid, ethanol, or a combination thereof.

In some embodiments, the hypotonic solution comprises one or more organic or inorganic buffers, one or more antibiotics or antimycotics, an alkaline pH, and wherein the osmolarity of the solution is maintained as hypotonic to cells.

In some embodiments, the first surfactant solution comprises a salt selected from the group consisting of KCl and NaCl, one or more organic or inorganic buffers, one or more antibiotics or antimycotics, an alkaline pH, one or more protease inhibitors, and 0.2-3% (v/v) of a anionic, non-ionic, zwitterionic or cationic detergent selected from the group consisting of Triton X-100, Triton X-200, Tween 20, Tween 80, sodium deoxycholate, CHAPS, sodium dodecyl sulfate (SDS), N-lauroyl-sarcosinate, Igepal CA630, and Sulfobetain-10 and -16). In some embodiments, the first surfactant solution is a >1 M saline solution. In some embodiments, the first surfactant solution comprises an anionic surfactant. In some embodiments, the anionic surfactant is Triton X-100®.

In some embodiments, the nuclease enzyme solution comprises an endonuclease selected from the group consisting of DNAse, RNAse, and Benzonase, wherein the solution is prepared with a physiological buffer selected from the group consisting of Hanks' Balanced Salt Solution (HBSS), HEPES, Phosphate Buffered Saline (PBS), Tris-Buffered Saline (TBS), and wherein the solution is maintained at a pH of 6-8. In some embodiments, the nuclease enzyme is DNase, RNase, or a combination thereof.

In some embodiments, the cleaning solution comprises 0.2-3% (v/v) of an anionic, non-ionic, zwitterionic or cationic detergent selected from the group consisting of Triton X-100, Triton X-200, Tween 20, Tween 80, sodium deoxycholate, CHAPS, sodium dodecyl sulfate (SDS), N-lauroyl-sarcosinate, Igepal CA630, and Sulfobetain-10 and -16 or Tri-n-butyl phosphate (TnBP), one or more organic or inorganic buffers, one or more antibiotics or antimycotics, an alkaline pH, and wherein the solution is prepared in either an aqueous or a 70% ethanol solvent. In some embodiments, the cleaning solution further comprises TRIZMA® base. In some embodiments, the cleaning solution further comprises about 70% ethanol. In some embodiments, the cleaning solution further comprises tri-n-butyl phosphate (TnBP).

In some embodiments, the method further comprises carrying out one or more steps at a temperature of between about 22° C. and 40° C. In some embodiments, the contacting of the enzyme-treated tissue with the cleaning solution is carried out at about 22° C.

In some embodiments, the human tissue is a human skin tissue. In some embodiments, the human tissue is a soft human tissue. In some embodiments, the soft human tissue is a heart valve, tendon, ligament, artery, vein, diaphragm, pericardium, fascia, dura mater, tympanic membrane, aortic conduit, or cartilage. In some embodiments, the human tissue is human allogeneic skin.

In some embodiments, the decellularized tissue is substantially decellularized. In some embodiments, the decellularized tissue is at least 90% decellularized. In some embodiments, the decellularized tissue is at least 95% decellularized. In some embodiments, the decellularized tissue is characterized by a substantial absence of positive staining for cell nuclei. In some embodiments, the decellularized tissue is characterized by a substantial absence of cellular DNA. In some embodiments, the decellularized tissue is characterized by a substantial absence of one or more immunogenic proteins. In some embodiments, the immunogenic protein is HLA-DR or HLA-A,B,C.

In some embodiments, the bioprosthetic tissue is characterized by a substantial absence of pathogens and spores. In some embodiments, the decellularized tissue is characterized by greater than 70-80% reduction in cytoskeletal proteins levels. In some embodiments, the cytoskeletal proteins are vimentin, beta-actin, alpha-actin, myosin, tubulin, and vinculin. In some embodiments, the bioprosthetic tissue includes dermis.

Also described herein is a bioprosthetic tissue produced using one or more methods described herein.

Also described herein is a tissue, wherein the tissue is substantially free of nucleic acids. Also described herein is a tissue, wherein the tissue is substantially free of one or more major histocompatibility molecules (MHC). Also described herein is a tissue, wherein the tissue is substantially free of *staphylococcus* bacteria. Also described herein is a tissue, wherein the tissue is substantially free of *streptococcus* bacteria. Also described herein is a tissue, wherein the tissue is substantially free of *enterococcus* bacteria. Also described herein is a tissue, wherein the tissue is substantially free of *bacillus* bacteria. Also described herein is a tissue, wherein the collagen structure of the tissue is not substantially altered following treatment using a method described herein as compared to a fresh control tissue.

In some embodiments, a tissue described herein is substantially free of *Staphylococcus aureus* bacteria. In some embodiments, a tissue described herein is substantially free of *Streptococcus pyogenes* bacteria. In some embodiments, a tissue described herein is substantially free of *Enterococcus* bacteria. In some embodiments, a tissue described herein is substantially free of *Bacillus subtilis*. In some embodiments, a tissue is substantially free of fungus.

In some embodiments, a tissue described herein is human skin.

In some embodiments, the nucleic acid is DNA or RNA. In some embodiments, the nucleic acid is RNA. In some embodiments, the nucleic acid is DNA. In some embodiments, a tissue described herein has less than 0.5 ng/mg dry weight of tissue of DNA. In some embodiments, a tissue described herein has less than 0.5 ng/mg dry weight of tissue of DNA as measured by a PicoGreen® DNA Assay.

In some embodiments, the MHC is HLA-DR. In some embodiments, a tissue is substantially free of HLA-DR as measured by immunohistochemistry. In some embodiments, the MHC is HLA-A,B,C. In some embodiments, a tissue is substantially free of HLA-A,B,C as measured by immunohistochemistry.

In some embodiments, a tissue is substantially free of Vimentin as measured by immunohistochemistry. In some embodiments, a tissue is substantially free of Beta-Actin as measured by immunohistochemistry.

In some embodiments, a tissue comprises elastin as measured by histology using Van Gieson stain. In some embodiments, a tissue comprises one or more proteoglycans as measured by histology using Masson's Trichrome stain.

In some embodiments, the collagen structure of a bioprosthetic tissue is not substantially altered compared to a fresh control tissue as assessed by the thermal stability of collagen. In some embodiments, the denaturation temperature of a bioprosethetic tissue is not substantially altered compared to a fresh control tissue. In some embodiments, the denaturation temperature of a bioprosthetic tissue is about 64 to 68° C. as measured by a Hydrothermal Isometric Tension (HIT) test.

Also described herein is a kit comprising one or solutions described herein. In some embodiments, the kit comprises a hyptotonic solution. In some embodiments, the kit comprises a first surfactant solution, a nuclease enzyme solution. In some embodiments, the kit comprises a cleaning solution. In some embodiments, the kit comprises a bioburden reducing agent solution. In some embodiments, the kit includes instructions for use of the kit and its contents. In some embodiments, the kit includes a sterile container. In some embodiments, the kit includes labeling with directions for use. In some embodiments, the kit comprises instructions for contacting a human tissue with one or more of the solutions described herein. In some embodiments, the kit further comprises a tissue described herein. In some embodiments, the tissue is an untreated tissue. In some embodiments, the kit further comprises instructions for performing a method described herein.

Also described herein is a kit, comprising a bioprosthetic tissue described herein or a tissue described above. In some embodiments, the kit includes instructions for using the tissue. In some embodiments, the kit includes instructions for use of the kit and its contents. In some embodiments, the kit includes a sterile container. In some embodiments, the kit includes labeling with directions for use. In some embodiments, the kit further comprises instructions for transplanting the tissue into a subject in need thereof. In some embodiments, the kit comprises a hyptotonic solution. In some embodiments, the kit comprises a first surfactant solution, a nuclease enzyme solution. In some embodiments, the kit comprises a cleaning solution. In some embodiments, the kit comprises a bioburden reducing agent solution. In some embodiments, the kit comprises instructions for contacting a human tissue with one or more of the solutions described herein. In some embodiments, the kit further comprises instructions for performing a method described herein.

DETAILED DESCRIPTION

Figure 1:
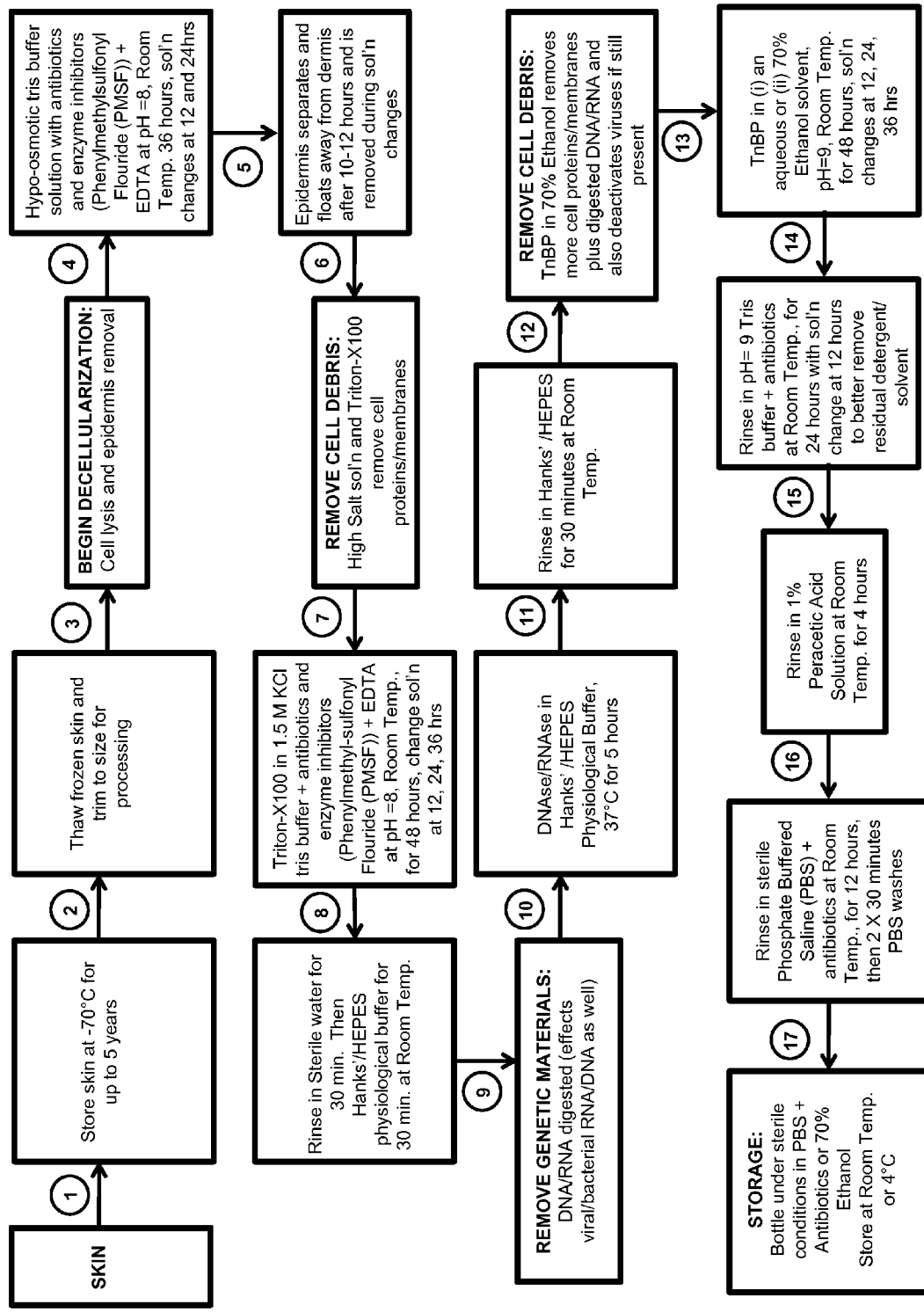
FIG. 1. Flowchart outlining the steps in one embodiment of the decellularization process for human skin.

Decellularization technology is a method that has the potential to revolutionize tissue allograft transplantation. Decellularization involves extracting cellular materials (the source of immune response and viruses) from allograft tissues leaving an intact, structurally native extracellular matrix scaffold comprised of collagen, elastin, and proteoglycans. Moreover, the decellularization process as described herein gives rise to safer and more sterile grafts by eliminating bacteria and viruses.

The description relates to preferred aspects by way of illustration only. It should be noted that from the following discussion, alternative aspects disclosed herein will be readily recognized as viable alternatives that can be employed without departing from the principles of what is claimed. It should be noted that the language used herein has been principally selected for readability and instructional purposes, and it can not have been selected to delineate or circumscribe the inventive subject matter. Accordingly, the present disclosure is intended to be illustrative, but not limiting, of the scope of claimed methods.

As used in this specification and the appended claims, the singular forms "a", "an" and "the" include plural referents unless the content clearly dictates otherwise. Thus, for example, reference to "a decellularized tissue" includes a combination of two or more decellularized tissues, and the like.

As used herein any reference to "one aspect" or "an aspect" means that a particular element, feature, structure, or characteristic described in connection with the aspect is included in at least one aspect. The appearances of the phrase "in one aspect" in various places in the specification are not necessarily all referring to the same aspect.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Deoxyribonucleic acid (DNA) in the majority of organisms is the genetic material while ribonucleic acid (RNA) is involved in the transfer of information contained within DNA into proteins. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The terms "polypeptide," "protein," and "peptide" are used interchangeably herein. It is well-known in the art of protein biochemistry that amino acids, the 'building blocks' of proteins, have particular sizes and characteristics, such as charge, hydrophobicity and hydrophilicity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

In certain aspects, the present disclosure provides for tissue that is substantially free of some component (e.g., one or more cytoskeletal proteins, MHC molecules, or pathogens such as bacteria and viruses). As used herein, the term "substantially free" means that the presence of a particular component is either not detected using known assays, or if it is detected, it is only present in an amount that is in accordance with the tissue regulations of the U.S. Food and Drug Administration (FDA) as set forth in Title 21 Code of Federal Regulations (CFR), Parts 1270 and 1271, herein incorporated by reference. In various aspects, "substantially free" can include a tissue that is about 90%, 90%, 91%, 92%, 93%, 94%, 95%, 96%, 97%, 98%, or 99% free of a component. In certain aspects, "substantially free" means that the tissue is completely free of the component. In certain aspects, "substantially free" means that the tissue is 100% free of the component.

As used herein, a tissue that is "substantially free of a pathogen" or "substantially free of pathogens" and similar terminology about a specific pathogen or class of pathogens means a tissue that complies with American Association of Tissue Banks (AATB) Standards for Tissue Banking under K2.200.

The term "decellularization" refers to the removal and/or extraction of cells and/or cellular components from a tissue.

In certain aspects, the present disclosure provides for tissue that is substantially decellularized. As used herein "substantially decellularized" means that the tissue is 70%, 75%, 80%, 85%, 90%, 91%, 92%, 93%, 94%, 95%, 96%, 97%, 98%, or 99% free of cells. In certain aspects, "substantially decellularized" means that the tissue is completely free of cells. In certain aspects, "substantially decellularized" means that the tissue is 100% free of cells.

The term "human bioprosthetic tissue" refers to a human tissue that has been substantially decellularized. In some embodiments, the human bioprosthetic tissue has also been sterilized.

The phrase "cellular component," as used herein, refers to substances that constitute a portion of a cell, including cell membranes and macromolecules that are normally found enclosed within a cell membrane, embedded within a cell membrane, or attached to a cell membrane.

Any terms not directly defined herein shall be understood to have the meanings commonly associated with them as understood within the art of the present disclosure. Certain terms are discussed herein to provide additional guidance to the practitioner in describing the compositions, devices, methods and the like of aspects of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the present disclosure herein.

Methods

In certain aspects, the decellularization methods of the present disclosure involve a series of progressively more sterile wash steps that include variations between hypoosmotic and hyperosmotic conditions, surfactant, enzyme, and physiological buffer solutions. FIG. 1 provides a general flowchart that is representative of the methods of one embodiment of the present disclosure. Each stage of the process is designed to sequentially break down and remove cellular components while preventing the degradation or disruption of extracellular matrix components.

According to certain aspects of the present disclosure, hypoosmotic conditions are first applied to burst cells. When the sample comprises skin, these conditions also serve to gently remove the epidermal cellular layer while leaving the underlying basement membrane matrix intact. In certain aspects, a second solution is applied, wherein that solution comprises a high salt content and surfactant (e.g., Triton-X100®). This second solution is utilized to solubilize and remove cytoplasmic and cytoskeletal components. In further aspects, cellular genetic materials are then degraded using endonucleases (e.g., DNAse, RNAse) which can also attack bacteria and viruses. In further aspects, tissues can subsequently be treated with a solution comprising a chaotropic agent and/or a surfactant to further removed any residual disrupted cellular materials. In certain aspects, that solution comprises tri-n-butyl phosphate (TnBP), a chaotropic agent that disrupts hydrogen and hydrophobic bonds. TnBP is also known to improve sterility by deactivating and removing viral proteins from blood products (Horowitz et al., Blood, 79(3):852-831 (1992)). Certain aspects of the present disclosure involve the additional step of washing the tissue as sufficient to provide residual surfactant levels far below cellular toxicity levels (Gratzer et al., Tissue Engineering, 12(10):2975-2983 (2006)).

Although certain methods are asserted to provide tissue decellularization, the present disclosure describes one of the first known methods actually giving rise to substantially complete decellularization. Most decellularization processes can be classified as a physically-based process, a chemically-based process, or a biochemically-based process. There are many protocols that borrow from several of these process classifications and interpretation of the effects of decellularization on the extracellular matrix becomes more difficult as the complexity of the protocols increases.

The present disclosure relates in some aspects to a method of rendering a tissue acellular. In various aspects of the present disclosure, decellularization can be accomplished using a number of chemical treatments, including incubation in certain salts, detergents or enzymes. The method comprises exposing the tissue to a hypotonic solution under conditions such that cell lysis results, and subjecting the resulting tissue to nuclease treatment so as to remove nucleic acids and associated phosphorous-containing groups. Nuclease treatment effectively stops cell replication and protein synthesis.

In some aspects, a method for producing a human bioprosthetic tissue is described herein. In some aspects the method includes contacting a human tissue with a hypotonic solution to produce a lysed tissue. In some aspects the method includes contacting the lysed tissue with a first surfactant solution to produce a surfactant-treated tissue. In some aspects the method includes contacting the surfactant-treated tissue with a nuclease enzyme solution to produce an enzyme-treated tissue. In some aspects the method includes contacting the enzyme-treated tissue with a cleaning solution comprising a second surfactant, a chaotropic agent, or a mixture thereof, to produce a decellularized tissue. In some aspects the method includes contacting the decellularized tissue with a bioburden reducing agent solution to produce the human bioprosthetic tissue.

In some aspects the method includes contacting a human tissue with a hypotonic solution to produce a lysed tissue. As used herein, "hypotonic solution" means an aqueous solution with a salt concentration lower than that found in normal cells of the body (e.g., <300 mOsm). A hyptonic solution is generally designed to (i) cause the cells in the tissue to absorb water (hypotonic conditions) and eventually burst and (ii) cause the intact epidermal layer of a tissue to separate from the underlying dermis while leaving the basement membrane intact. Thus, a hyptonic solution can be any aqueous solution with a salt concentration less than that found in normal cells (i.e. <300 mOsm) that causes cell swelling. A hyptonic solution can include one or more organic or inorganic buffers, an alkaline pH, one or more antibiotics/antimycotics, one or more protease inhibitors, and osmolarity maintained that is hypotonic to cells. In some aspects, alkaline pH helps to limit protease activity, where desired.

In some aspects the method includes contacting a human tissue with a first surfactant solution to produce a surfactant-treated tissue. As used herein "first surfactant solution" means a solution including an anionic, non-ionic, zwitterionic, and/or cationic detergent. An anionic, non-ionic, zwitterionic, and/or cationic detergent can include Triton X-100, Triton X-200, Tween 20, Tween 80, sodium deoxycholate, CHAPS, sodium dodecyl sulfate (SDS), N-lauroyl-sarcosinate, Igepal CA630, and/or Sulfobetain-10 and -16. In some aspects the first surfactant solution can be a high saline (e.g., >1M), buffered solution at an alkaline pH (e.g., pH=8-10) containing 0.2-3% (v/v) of the anionic, non-ionic, zwitterionic or cationic detergent. In some aspects the first surfactant solution can include salt (e.g., KCl, NaCl), one or more organic or inorganic buffers, one or more antibiotics/antimycotics, one or more anionic, non-ionic, zwitterionic or cationic detergents and one or more protease inhibitors. The first surfactant solution is generally designed to remove cell membranes and cytoskeletal components. Alkaline pH helps to limit protease activity, where desired.

The use of the detergent Triton X-100® has been demonstrated to remove cellular membranes, as detailed in U.S. Pat. No. 4,801,299. Other acceptable decellularizing detergents include polyoxyethylene (20) sorbitan mono-oleate and polyoxyethylene (80) sorbitan mono-oleate (TWEEN 20® and 80), sodium deoxycholate, 3-[(3-chloramidopropyl)-dimethylammino]-1-propane-sulfonate, octyl-glucoside and sodium dodecyl sulfate. In some aspects, a detergent can include octylphenol ethylene oxide condensate.

In some aspects the method includes contacting a human tissue with a nuclease enzyme solution to produce an enzyme-treated tissue. As used herein the term "enzyme" refers to a protein-based biocatalyst. An enzyme can generally be used to breakdown nucleic and ribonucleic acids. Enzymes can include nucleases such as endonucleases (e.g., DNAse, RNAse, Benzonase). In some aspects, Deoxyribonuclease I is from bovine pancreas (Bos Taurus) (NM_174534.2; NP_776959.1). In some aspects, Ribonuclease A is from bovine pancreas (Bos Taurus) (NM_181810.1; NP_861526.1).

In certain aspects, enzymes can be used to accomplish decellularization, including but not limited to dispase II, trypsin, and thermolysin. These enzymes react with different components of collagen and intercellular connections in achieving their effects. Dispase II attacks Type IV collagen, which is a component of the lamina densa and anchoring fibrils of the basement membrane. Thermolysin attacks the bulbous phemphigoid antigen in the hemidesmosome of the basal layer of keratinocytes. Trypsin attacks the desmosome complex between cells. Due to the proteolytic nature of these enzymes, care must be taken that cellular removal occurs without significant damage to the extracellular matrix, including the basement membrane complex. This is a function of concentration, time and temperature. If used for too long a time or at too high a concentration, dispase II for example can completely remove the basement membrane complex from the dermis.

In some aspects the method includes contacting a human tissue with a cleaning solution comprising a second surfactant, a chaotropic agent, or a mixture thereof, to produce a decellularized tissue. As used herein the term "cleaning solution" means a solution that includes an anionic, non-ionic, zwitterionic and/or cationic detergent or a chaotropic agent. An anionic, non-ionic, zwitterionic and/or cationic detergent can include Triton X-100, Triton X-200, Tween 20, Tween 80, sodium deoxycholate, CHAPS, sodium dodecyl sulfate (SDS), N-lauroyl-sarcosinate, Igepal CA630, and/or Sulfobetain-10 and -16. As used herein "chaotropic agent" means a substance that increases the transfer of apolar groups to water because of its ability to decrease the 'ordered' structure of water and to increase its lipophilicity. A chaotropic agent generally causes the dissolution of biological membranes, the solubilization of particulate proteins, changes in the secondary, tertiary, and quaternary structure of proteins, and denaturation of nucleic acids. A chaotropic agent can include Tri-n-butyl phosphate (TnBP), ions (e.g. $SCN^-$, CNS, $ClO_4^-$, $I^-$, $Br^-$, $CH_3$—$COO^-$), urea derivatives, gaunidine derivatives. In some aspects a cleaning solution can include one or more organic or inorganic buffers, one or more antibiotics/antimycotics, an alkaline pH, and the solution is prepared in sterile water or 70% ethanol as the solvent. In some aspects a cleaning solution can include 0.2-3% (v/v) of an anionic, non-ionic, zwitterionic or cationic detergent or a chaotropic agent, one or more organic or inorganic buffers, one or more antibiotics/antimycotics, an alkaline pH, and the solution is prepared in either an (i) aqueous or (ii) 70% ethanol solvent. The cleaning solution is generally designed to remove any remaining cellular components (e.g., cytoskeletal proteins, DNA, RNA fragments). As above, alkaline pH helps to limit protease activity, where desired.

In some aspects the method includes contacting a human tissue with an isotonic solution. As used herein "isotonic solution" means an aqueous solution with a salt concentration approximately equal or equal to that found in normal cells of the body. In some aspects, isotonic solutions can include Lactated Ringer's solution, Normal Saline solution (0.9%), and Phosphate Buffered Saline (PBS).

In some aspects the method includes contacting a human tissue with a protease inhibitor. As used herein "protease inhibitor" means an agent that is capable of deactivating enzymes that are capable of degrading proteins. Protease inhibitors can include phenylmethanesulfonylfluoride (PMSF), aprotinin, leupeptin, and Ethylenediaminetetraacetic acid (EDTA).

In various aspects, protease inhibitors are employed in combination with other reagents to prevent degradation of the extracellular matrix. Collagen-based connective tissues contain proteases and collagenases as endogenous enzymes in the extracellular protein matrix. Additionally, certain cell types including smooth muscle cells, fibroblasts and endothelial cells contain a number of these enzymes inside vesicles called lysosomes. When these cells are damaged by events such as hypoxia, the lysosomes are ruptured and their contents released. As a result, the extracellular matrix can undergo severe damage from protein, proteoglycan and collagen breakdown. This damage can be severe, as evidenced in clinical cases of cardiac ischemia where a reduction in oxygen which is insufficient to cause cell death results in pronounced damage to the collagen matrix. Additionally, a consequence of extracellular breakdown is the release of chemoattractants, which solicit inflammatory cells, including polymorphonuclear leukocytes and macrophages, to the graft, which are intended to remove dead or damaged tissue. These cells also, however, perpetuate the extracellular matrix destruction through a nonspecific inflammatory response. Accordingly, the processing solution contains one or more protease inhibitors selected from the group of N-ethylmaleimide (NEM), phenylmethylsulfonylfluoride (PMSF) ethylenediamine tetraacetic acid (EDTA), ethylene glycol-bis-(2-aminoethyl(ether)NNN'N'-tetraacetic acid, ammonium chloride, elevated pH, apoprotinin and leupeptin to prevent such damage.

In some aspects the method includes contacting a human tissue with a bioburden reducing agent solution. As used herein "bioburden reducing agent" means an agent that can inactivate, destroy, or eliminate infectious materials (e.g., bacteria, spores, fungi, mold, or viruses). Bioburden reducing agents can include an antibacterial agent, an alcohol (e.g., methyl, ethyl, propoyl, isopropyl, butyl, t-butyl), an antiviral agent, an antimycotic agent, chlorine dioxide, a detergent, antimicrobials, antifungal agents, hydrogen peroxide, sodium hydroxide, and/or peracetic acid. See also U.S. Pat. No. 5,460,962, herein incorporated by reference.

The solutions of the present disclosure may optionally comprise an appropriate buffer. The buffer can involve one of many different organic buffers. In certain aspects, an organic buffer is selected from the group consisting of 2-(N-morpholino)ethanesulfonic acid (MES), Tris (hydroxymethyl)aminomethane (TRIS) and (N-[2-hydroxyethyl]piperazine-N'-[2-ethanesulfonic acid] (HEPES). Alternatively, a low salt or physiological buffer including phosphate bicarbonate acetate citrate glutamate with or without glycine, can be more appropriate in certain applications.

In some aspects, one or more of the solutions used in the presently disclosed methods further comprise at least one protease inhibitor. In certain aspects, the protease inhibitor is a serine protease inhibitor, metalloprotease inhibitor, or a combination thereof. In some aspects, one or more of the solutions used in the presently disclosed methods comprises at least one enzyme. In certain aspects, that enzyme is DNase, RNase, or a combination thereof. In some aspects, one or more of the solutions used in the presently disclosed methods comprises a surfactant. In certain aspects, that surfactant is an anionic surfactant. In further aspects, the anionic surfactant is Triton X-100®. In some aspects, one or more of the solutions used in the presently disclosed methods further comprises TRIZMA® base. In further aspects, the present disclosure provides methods for producing a bioprosthetic tissue, the method further comprising sonicating the tissue. In some aspects, one or more of the solutions used in the presently disclosed methods further comprises tri-n-butyl phosphate (TnBP). In some aspects, one or more of the solutions used in the presently disclosed methods further comprises about 70% ethanol.

In certain aspects, a combination of physical treatments and chemical or biochemical treatments can be used for tissue decellularization.

In certain aspects, cells are lysed physically using osmotic gradients, mechanical compression/massage, or freeze-thaw cycles. Hypertonic and hypotonic treatments put hydrostatic pressure on cell membranes in an aqueous environment causing them to burst and release their cell contents. The contents of the cell are then more accessible to later treatments with detergents or isotonic washout procedures. Mechanical compression or massage can be used to encourage membrane degradation and gradually expose more cell membranes to extraction solutions. Freeze-thaw cycles can be used to kill cells and then fracture their cell membranes so that subsequent washout procedures can access internal cell contents and fragmented membranes.

In further aspects, the method includes carrying out one or more steps at a temperature of between about 20° C. and 40° C. In further aspects, one or more steps of the method is carried out at about 30° C. In further aspects, one or more steps of the method is carried out at room temperature. In further aspects, one or more steps of the method is carried out at 37° C. In further aspects, one or more steps of the method is carried out at 22° C. In further aspects, one or more steps of the method is carried out at less than 20, about 20, 20, 21, 22, 23, 24, 25, 26, 27, 28, 29, 30, 31, 32, 33, 34, 35, 36, 37, 38, 39, 40, about 40, or more than 40° C.

In some aspects, tissues are harvested and prepared for treatment. The extent of tissue preparation is dependant upon the tissue to be treated, but usually involves removing extraneous tissue elements and cutting the tissue to size in order to facilitate decellularization.

In some aspects, a tissue is immersed in a hypotonic salt (<300 mOsm) solution with a pH=7-9 (e.g., about 7, 7, about 8, 8, 9, or about 9), with anti-proteolytic agents whose concentration are dependant upon inhibitor used (e.g., phenylmethanesulfonylfluoride (PMSF), aprotinin, leupeptin, Ethylenediaminetetraacetic acid (EDTA)), anti-microbial agents (e.g., penicillin, vancomycin, streptomycin, gentamycin, kanamycin, neomycin, sodium azide ($NaN_3$)) with or without anti-fungal agents (e.g., Amphotericin B, Nystain) prepared with a type II cell culture grade deionized water. The tissue can be treated with a minimum volume ratio of solution to tissue of 20:1, 30:1, 40:1, or 50:1 (e.g., 20:1-50:1), on a rotating shaker table at 40-65 RPM, for 24-48 hours, T=4-40° C., with solution changes occurring at 12 hour intervals.

In certain aspects, the tissue is then transferred to a high saline (>1 M, NaCl, KCl) buffered solution (pH=8-10) containing 0.2-3% (v/v) of a anionic, non-ionic, zwitterionic or cationic detergent (e.g., Triton X-100®, Triton X-200®, TWEEN 20®, TWEEN 80®, sodium deoxycholate, CHAPS, sodium dodecyl sulfate (SDS), N-lauroyl-sarcosinate, Igepal CA630, Sulfobetain-10 and -16) and protease inhibitors (e.g., phenylmethanesulfonylfluoride (PMSF), aprotinin, leupeptin, Ethylenediaminetetraacetic acid (EDTA)) prepared with a type II cell culture grade deionized water. The tissue is treated with a volume ratio of solution to tissue of 20:1, 30:1, 40:1, or 50:1 (e.g., 20:1-50:1), on a rotating shaker table at 40-65 RPM, for 24-48 hours, T=4-40° C., with solution changes occurring at 12 hour intervals.

In further aspects, the tissue can then be subjected to rinses with sterile physiological buffer (e.g., Hanks' Balanced Salt Solution (HBSS), HEPES, Phosphate Buffered Saline (PBS), Tris-Buffered Saline (TBS)) pH=6-8, T=4-40° C., 5 minutes to 1 hour, and then treated with a solution of endonucleases (e.g., DNAse, RNAse, Benzonase) prepared in a physiological buffer (e.g., Hanks' Balanced Salt Solution (HBSS), HEPES, Phosphate Buffered Saline (PBS), Tris-Buffered Saline (TBS)), pH=6-8, for 1-5 hours, T=20-40° C. Afterward, the tissue is rinsed in sterile physiological buffer alone as specified above for 5 minutes-1 hour, T=4-40° C.

In additional aspects, the tissue is treated with a sterile solution of 0.2-3% (v/v) anionic, non-ionic, zwitterionic or cationic detergent (e.g., Triton X-100®, Triton X-200®, TWEEN 20®, TWEEN 80®, sodium deoxycholate, CHAPS, sodium dodecyl sulfate (SDS), N-lauroyl-sarcosinate, Igepal CA630, Sulfobetain-10 and -16) or chaotropic agent (e.g., Tri-n-butyl phosphate (TnBP)) prepared in either (i) physiological buffer solution (Hanks' Balanced Salt Solution (HBSS), HEPES, Phosphate Buffered Saline (PBS), Tris-Buffered Saline (TBS)) adjusted to pH=7-9 with anti-microbial agents (e.g., penicillin, vancomycin, streptomycin, gentamycin, kanamycin, neomycin, sodium azide ($NaN_3$)) with or without anti-fungal agents (Amphotericin B, Nystain) or with (ii) 50-70% ethanol, for 24-48 hours at T=4-40° C. Afterward, the tissue is rinsed with a sterile 50 mM Tris buffer solution adjusted to pH 9 (containing no detergent or chaotropic agent) for 12-24 hours at T=4-40° C.

In further aspects, the tissue is treated with a 0.05-3% (v/v) Peracetic Acid (PAA) solution in ethanol or Phosphate Buffered Saline (PBS) neutralized to pH=7 to 7.5, for a duration of 30 minutes to 4 hours at T=20-40° C. After, the tissue can be rinsed with sterile physiological buffer (e.g., Hanks' Balanced Salt Solution (HBSS), HEPES, Phosphate Buffered Saline (PBS), Tris-Buffered Saline (TBS)) with anti-microbial agents (e.g., penicillin, vancomycin, streptomycin, gentamycin, kanamycin, neomycin, sodium azide ($NaN_3$)) with or without anti-fungal agents (e.g., Amphotericin B, Nystain) for 12-24 hours at T=4-40° C.

In further aspects, tissues can be bottled under sterile conditions in either (i) sterile physiological buffer (e.g., Hanks' Balanced Salt Solution (HBSS), HEPES, Phosphate Buffered Saline (PBS), Tris-Buffered Saline (TBS)) with anti-microbial agents (e.g., penicillin, vancomycin, streptomycin, gentamycin, kanamycin, neomycin, sodium azide ($NaN_3$)) with or without anti-fungal agents (e.g., Amphotericin B, Nystain) or (ii) 50-70% ethanol and stored at T=4-25° C.

In some aspects, human skin is procured and prepared for treatment. The extent of tissue preparation is dependent upon the quality of the skin obtained, but usually involves removing extraneous tissue elements and cutting the tissue to size(s) required by end users. For this example, three specimens of human skin are treated in one container. The size of the specimens used is 4 cm×5 cm and tissues are treated with a volume ratio of solution to tissue of 50:1.

In some aspects, specimens are transferred to a lidded polypropylene jar containing a preferred volume of 300 mL of a hypotonic (<300 mmol/L preferred value of 10 mM) Tris buffer and a metalloprotease inhibitor at a concentration of 1 μM-25 mM (preferred value of 5 mM and inhibitor being used is ethylenediaminetetraacetic acid (EDTA)). This solution is adjusted to pH 7-9 (preferred at pH=8) using HCl/NaOH prior to use. To this container can be added antibiotics/antimycotics at 50-100 U/mL or 50-100 μg/mL dependent upon agent (preferred using 5 mL/L of a penicillin/streptomycin 100× solution with a stock concentration of 10,000 U/mL/10,000 mg/mL) and protease inhibitor (preferred value of 0.35 mL/L of the serine protease inhibitor (5% phenylmethanesulfonyl fluoride in 100% ethanol)). The container is allowed to mix gently on a shaker table at 40-65 RPM, T=20-25° C., for 24 hours with fresh solution changed at 12 hours. This stage is designed to (i) cause the cells in the tissue to absorb water (hypotonic conditions) and eventually burst and (ii) cause the intact epidermal layer to separate from the underlying dermis while leaving the basement membrane intact.

In some aspects, the previous hypotonic solution is decanted and replaced with a minimum volume ratio of solution to tissue of 50:1 (preferred 300 mL) of a high saline solution (preferred value of 1.5 M of potassium chloride with 50 mM Tris buffer) containing 1% (v/v) Triton X-100 (octyl phenoxy polyethoxyethanol), metalloprotease inhibitor at a concentration of 1 µM-25 mM (preferred value of 5 mM of EDTA) and protease inhibitor (preferred value of 0.35 mL/L of the serine protease inhibitor (5% phenylmethanesulfonyl fluoride in 100% ethanol)). To the container is added antibiotics/antimycotics at 50-100 U/mL or 50-100 µg/mL dependent upon agent (preferred using 5 mL/L of a penicillin/streptomycin 100× solution with a stock concentration of 10,000 U/mL/10,000 mg/mL). The container is allowed to mix gently on a shaker table (at 40-65 RPM), T=20-25° C., for 36 hours with fresh solution changed every 12 hours. This stage of the treatment is designed to remove cell membranes and cytoskeletal components.

In some aspects, the previous high saline solution is decanted and replaced with a volume ratio of solution to tissue of 50:1 (preferred value of 300 mL) of sterile deionized water. Specimens are rinsed for 30 minutes. Following the rinse with sterile deionized water, it is replaced with a volume ratio of solution to tissue of 50:1 (preferred value of 300 mL) of Hanks'/HEPES physiological buffer (0.14 M Sodium Chloride, 5.4 mM Potassium Chloride, 0.26 mM Sodium Phosphate dibasic, 0.44 mM Potassium Phosphate monobasic, 4.2 mM Sodium Bicarbonate, 10 mM HEPES Sodium salt, 8.3 mM Calcium Chloride dihydrate, 0.2 mM Magnesium Sulfate heptahydrate, and 0.25 mM Magnesium Chloride hexahydrate. This solution is adjusted to pH 7.35 using 2 M HCl/NaOH prior to use). Specimens are rinsed in physiological buffer for 30 minutes.

In some aspects, following this rinse, the physiological buffer is decanted and replaced with 200 mL of Hanks'/HEPES physiological buffer. To this is added endonucleases, preferred DNAse and RNAse, at preferred quantities of 1330 µL of deoxyribonuclease stock (type II from bovine pancreas, 13.3 U/µL NaCl/glycerol pH 7.3 solution and 1330 µL of ribonuclease stock (type III-A from bovine pancreas, 85 µg/mL). The tissue is then placed in a shaking water bath, gently mixed (45-60 RPM) at 37° C. for 5 hours. After 5 hours the solution is decanted and replaced with fresh Hanks'/HEPES physiological buffer, briefly rinsing the tissue. This stage of the process is designed to degrade DNA and RNA to facilitate their subsequent removal.

In some aspects, the previous physiological buffer rinse is decanted and replaced by 300 mL of a 50 mM Tris buffer solution adjusted to pH 9 and containing 1% (v/v) Tri-n-butyl phosphate (TnBP). To the container is then added 1.5 mL of a penicillin/streptomycin antibiotic/antimycotic 100× solution (stock concentration of 10,000 U/mL/10,000 mg/mL). This step of the decellularization treatment can also be performed using a solution made up as 1% (v/v) TnBP in 70% ethanol without antibiotics/antimycotics. The tissue then gently mixed on a shaker table (45-60 RPM) at T=20-25° C. for 48 hours with fresh solution changes every 12 hours. This stage is designed to further remove any remaining cellular components (cytoskeletal proteins, DNA, RNA) as TnBP is a "surfactant like" chaotropic solvent. Further, TnBP has been shown to deactivate viruses.

In some aspects, after treatment, the solution is decanted and refreshed with 300 mL of 50 mM Tris buffer solution adjusted to pH 9 (containing no TnBP). The same amount of antibiotic/antimycotic solution (penicillin/streptomycin) previous used is added and the container is allowed to mix gently on a shaker table (at 40-65 RPM), T=20-25° C., for 24 hours with fresh solution changed at 12 hours.

In some aspects, the previous pH 9 Tris buffer solution is decanted and replaced with 300 mL of a 1% (v/v) Peracetic Acid (PAA) solution in ethanol (PAA solution consisted of 2% peracetic acid, 100% ethanol, and sterile water (ratio v/v/v 2/1/1), providing a final sterilization solution of 1% PAA) for 4 hours, mixing gently on a shaker table (at 40-65 RPM), at T=20-40° C. After PAA treatment, fresh sterile phosphate-buffered saline solution (PBS, containing 0.14 M sodium chloride, 2.7 mM potassium chloride, 6.5 mM sodium phosphate dibasic, 1.5 mM potassium phosphate monobasic and is adjusted to pH 7.4). The same amount of antibiotic/antimycotic (penicillin/streptomycin) solution used previously is added and the container is allowed to mix gently on a shaker table (at 40-65 RPM), T=20-25° C., for 12 hours. After, the specimen is rinsed twice for 30 minutes each with 300 mL fresh sterile phosphate buffered saline solution at room temperature containing no antibiotics/antimycotics.

In some aspects, each piece of tissue is bottled under sterile conditions with a minimum volume ratio of solution to tissue of 20:1 to 50:1 in either (i) fresh sterile phosphate buffered saline solution infused with penicillin/streptomycin (6 mL/L of 100× solution with a stock concentration of 10,000 U/mL/10,000 mg/mL) solution or (ii) 70% ethanol and stored at 4° C.

Detergents

Critical to the success of many decellularization strategies are detergents or surfactants. Various detergents can be used according to the present methods. Detergents are useful for decellularization when they are added in a sufficient concentration to form micelles. A micelle is a cluster of detergent monomers, often spherical, that is oriented so that the non-polar domains of the detergent molecules are interacting internally, and the polar domains are interacting with water molecules externally. The concentration at which detergents form micelles is called the critical micelle concentration (CMC). The CMC varies with decellularization conditions, including ionic strength, pH, temperature and the presence of protein and lipids (including other detergent molecules). Micelles occupy space in the aqueous environment, and as such, must disrupt hydrogen bonds between water molecules. During decellularization, the extraction of cell components, including lipids and proteins from tissue, is accomplished when these micelles enter the tissue, dissolve non-polar components, and are washed out with solution changes.

Detergents can be classified by one of three designations: ionic, nonionic, and zwitterionic. Ionic detergents are either anionic or cationic, although cationic detergents are not used in decellularization processes due to their strong denaturing tendencies. A subgroup of ionic detergents are the bile acid salts, found in the intestine where they solubilize fats. Bile acids are milder than other anionic detergents such as SDS. Nonionic detergents, such as Triton X-100®, have neutral polar head groups and are non-denaturing to proteins. Nonionic detergents break lipid-lipid and lipid-protein interactions. Finally, zwitterionic detergents, such as CHAPS, have properties of both ionic and nonionic detergents. Zwitterionic detergents are generally milder than ionic detergents and more denaturing to proteins than nonionic detergents.

Solvents

Various solvents can be used according to the present methods for the disruption of protein and lipid interactions by destabilizing hydrophobic interactions. In some aspects, tri-n-butyl phosphate (TnBP) is used. An added benefit to the use of TnBP in a decellularization protocol is its proven anti-viral action (Horowitz et al., Blood, 79:826-831 (1992); Horowitz et al., Dev Biol Stand, 81:147-161 (1993)). In further aspects of the present methods, any other solvent showing good decellularization performance with very little damage to the extracellular matrix can be used (Woods, M Sc Thesis Dalhousie University, Halifax NS, Canada (2002); Woods et al., Biomaterials, 26:7339-7349 (2005)).

Protease Protection and Antibiotic/Anti-Viral Treatments

During decellularization, lysed cells release the contents of lysosomes into the extracellular space. Many of the enzymes released, especially proteases, are highly effective at degrading the extracellular matrix. One goal of decellularization is to preserve the intact extracellular matrix while removing cellular components, so the action of degradative enzymes is counterproductive. In various aspects of the present disclosure, protease inhibitors are present during the initial cell lysis phase of the procedure. In further aspects of the present disclosure, protease inhibitors are additionally present during subsequent phases of the decellularization process.

According to the present disclosure, protease inhibition can be achieved through a combination of methods. In certain aspects, lysosomal proteases are inhibited by using elevated pH (~pH 8). In further aspects, chelating agents that bind metallic enzyme cofactors such as magnesium, iron, or zinc (e.g., EDTA or 1,10 phenanthroline) are also used. In various aspects, chemical inhibition of proteases can be achieved by the addition of any one of a number of common protease inhibitors. Chemical inhibitors according to the present methods can include phenylmethanesulfonylfluoride (PMSF), aprotinin, or leupeptin. PMSF (irreversible binding) and aprotinin (reversible binding) inhibit serine proteases such as trypsin and chymotrypsin, whereas leupeptin (low stability in aqueous environments) inhibits both serine and cysteine proteases.

According to certain aspects of the present disclosure, methods are provided for the inhibition of bacteria. Inhibition of bacteria is beneficial in part because the decellularization process is not generally performed aseptically. In various aspects, common antibiotics used for decellularization treatments are used and can include gram positive bacteria cell wall synthesis inhibitors (e.g., penicillin or vancomycin), bacteria and mycoplasma protein synthesis inhibitors (e.g., streptomycin or gentamicin) and agents that induce ribosomal miscoding in gram positive/negative bacteria and mycoplasma (kanamycin). In further aspects, sodium azide ($NaN_3$) is also added to decellularization solutions to inhibit microbial growth.

In some aspects, one or more of the solutions used in the presently disclosed methods further comprises at least one bioburden reducing agent. In further aspects the bioburden reducing agent is penicillin, streptomycin, peracetic acid, or a combination thereof.

The use of allografts and xenografts is complicated by the potential for disease transmission. Many porcine tissues contain porcine endogenous retrovirus (PERV), even after decellularization (Leyh et al., J Thorac Cardiovasc Surg, 126:1000-1004 (2003); Walles et al., Eur J Cardiothorac Surg, 24:358-363 (2003)). Thus, in certain aspects, methods are provided for eliminating viruses. In further aspects, peracetic acid and/or ethanol treatments are used in conjunction with decellularization for the elimination of viruses (Hodde et al., Biotechnol Bioeng, 79:211-216 (2002)). In further aspects, the organic solvent TnBP is employed for the added purpose of diminishing the presence of viruses (e.g., human immunodeficiency virus (HIV)) (Horowitz et al., Blood, 79:826-831 (1992); Horowitz et al., Dev Biol Stand, 81:147-161 (1993)). In further aspects, anionic detergents have the effect of diminishing the presence of viruses (e.g., HIV and other enveloped viruses) (Luscher-Mattli, Antivir Chem Chemother, 11:249-259 (2000); Cserhati et al., Environment International, 28:337-348 (2002)). In certain aspects, the extracellular matrix is loaded with protease inhibitors, antibiotics, and antiviral agents at the end of the decellularization procedure.

Table A provides examples of a number of reagents and techniques that can be used according to the present disclosure along with their respective modes of action.

TABLE A

| | Mode of Action |
|---|---|
| PHYSICAL METHODS | |
| Osmotic Gradient | Bursts or contracts cells, disrupts cell membranes |
| Freeze/Thaw | Disrupts cell membranes |
| Mechanical Delamination | Separates tissue layers along natural planes of dissection |
| Agitation/Compression | Increases exposure of cell membranes to extraction solutions |
| CHEMICAL METHODS | |
| Anionic Detergents | |
| Bile Acid Salt | |
| Sodium Deoxycholate | Solubilizes phospholipids |
| | Disrupts protein-lipid interactions |
| | Generally non-denaturing, mild |
| Synthetic | |
| SDS (Sodium Dodecyl Sulfate) | Disrupts protein-protein interactions |
| | Denatures and solubilizes proteins |
| | Binds virus particles (incl. HIV) |
| Triton X-200 ® (alkylaryl polyether sulfonate) | Solubilizes cellular components |
| N-lauroyl-sarcosinate | Ruptures cells |
| | Solubilizes cell membrane proteins |

TABLE A-continued

| | Mode of Action |
|---|---|
| Nonionic Detergents | |
| Triton X-100 ® (PEG tert-octylphenyl ether) | Non-denaturing protein solubilization |
| Tween 20 ® or 80 ® (PEG-sorbitan monolaurate/oleate) | Solubilizes peripheral membrane proteins |
| Igepal CA630 (formerly sold as Nonidet P40) (Octylphenyl-PEG) | Non-denaturing protein solubilization |
| N-octyl-β-D glucopyranoside | Solubilization of membrane proteins |
| Zwitterionic Detergents | |
| Sulfobetain-10 and -16 | Help decrease micelle size with anionic detergents Retain zwitterionic nature over wide pH range |
| CHAPS | Disrupts protein-protein interactions Non-denaturing, forms small micelles |
| Alcohols | |
| Glycerol | Destroys bacteria Solubilizes cell components |
| Isopropanol | Disrupts cell membranes, dissolves lipids Destroys bacteria and viruses |
| Ethanol | Destroys bacteria |
| 1-Butanol | Extracts lipids |
| Organic Solvents | |
| Tri(n-butyl)phosphate (TnBP) | Disrupts protein-protein interactions, mild [65] Removes virus particles (incl. HIV) |
| Acids | |
| HCl, $H_2SO_4$ | Solubilize cells |
| Peracetic Acid | Destroys viruses, solubilizes cell remnants |
| Bases | |
| NaOH | Disrupt DNA/RNA, cell membranes Destroy viruses, inactivates prions [167] |
| $NH_4OH$ | Weakens lipid-protein bonds |
| Chelators | |
| EDTA | Bind to metallic cofactors, inhibiting enzymes |
| EGTA | Bind ions cells need to attach to substrates |
| BIOCHEMICAL METHODS | |
| Membrane/Attachment Enzymes | |
| Trypsin | Disrupts desmosomes, focal adhesions Cleaves peptide bonds on Arg and Lys |
| DISPASE DISPASE II | Attacks type IV collagen, helps lift cells |
| Phospholipase | Digests phospholipids in cell membranes |
| Antigen-targeted Enzymes | |
| Thermolysin | Attacks antigen in the hemidesmosome of the basal layer of keratinocytes. |
| α-galoctosidase | Digests α-1,3-galactose antigen |
| Exonucleases | |
| DNAse I | Facilitates hydrolysis of terminal DNA strands |
| RNAse A | Facilitates hydrolysis of terminal RNA strands |
| Endonucleases | |
| Benzonase | Facilitates degradation of internal bonds in DNA (single and double stranded) and RNA |

Tissues suitable for use in the present method include those appropriate for implantation. Tissues can be human in origin. The tissue is generally decellularized prior to any fixation. In certain aspects, the tissue may be a soft tissue. The decellularization method is applicable to various tissues, including heart valves, tendons, ligaments, arteries, veins, diaphragms, pericardium, fascia, dura mater, tympanic membranes, aortic conduits, dermis, cartilage, or any other suitable tissue.

According to one aspect, the present disclosure provides methods for producing a bioprosthetic tissue wherein the tissue is a human tissue.

According to one aspect, the present disclosure provides methods for producing a bioprosthetic tissue wherein the tissue is a soft tissue. In further aspects, the soft tissue is a heart valve, tendon, ligament, artery, vein, diaphragm, pericardium, fascia, dura mater, tympanic membrane, aortic conduit, dermis, or cartilage. In certain aspects, the tissue is dermis. In certain aspects, the tissue is human allogeneic skin.

Bioprostheses produced in accordance with the present disclosure can be used as replacements for defective tissues in mammals, particularly humans. Methods of effecting the replacement of, for example, heart valves, tendons, ligaments, vessels, etc., are well known in the art.

In certain aspects, the present methods are applied to the decellularization of skin. The current clinical use of partial thickness allograft skin is limited to a temporary bandage for the treatment of severe burns. Immune response in the patient results in the rejection of the skin and need for additional treatment and grafting procedures. The decellularization process would allow for prolonged cover and even host integration and remodeling. The elimination of "bioburden" significantly increases the supply of available skin for transplant.

Decellularization Assays

The extent of decellularization can be determined histochemically, for example, by staining the tissue with hematoxylin and eosin using standard techniques. Immunohistochemical staining can also be used, for example, to visualize cell specific markers such as Beta-actin and histocompatibility antigens—an absence of such markers being a further indication of decellularization. In certain aspects, immunohistochemical antibody staining can be used to identify specific immunogens associated with rejection (e.g., HLA-DR) and the removal of cellular DNA below the detection levels of current analysis methods.

In various aspects, the methods of the present disclosure yield tissue, wherein the tissue is characterized by a substantial absence of positive staining for cell nuclei.

In various aspects, the methods of the present disclosure yield tissue, wherein the tissue is characterized by a substantial absence of cellular DNA.

In various aspects, the methods of the present disclosure yield tissue, wherein the tissue is characterized by a substantial absence of immunogenic proteins. In further aspects, the immunogenic protein is HLA-DR. In further aspects, the immunogenic protein is HLA-A,B,C.

In various aspects, the methods of the present disclosure yield tissue, wherein the tissue is characterized by more than 70-80, 70, 80, 90, 95, or 99% reduction in cytoskeletal proteins levels. In further aspects, the cytoskeletal proteins are vimentin, beta-actin, alpha-actin, myosin, tubulin, and vinculin.

Tissue

Tissues suitable for use in the present method include those appropriate for implantation into humans. Tissues can be human in origin. The tissue is generally decellularized prior to any fixation or other use. In certain aspects, the tissue may be a soft tissue. Tissues can include skin, heart valves, tendons, ligaments, arteries, veins, diaphragms, pericardium, fascia, dura mater, tympanic membranes, aortic conduits, dermis, cartilage, or any other suitable tissue.

In some aspects, the tissue is a human tissue. In some aspects, the tissue is a soft tissue. In further aspects, the soft tissue is a heart valve, tendon, ligament, artery, vein, diaphragm, pericardium, fascia, dura mater, tympanic membrane, aortic conduit, dermis, or cartilage. In certain aspects, the tissue is dermis. In certain aspects, the tissue is human allogeneic skin.

Bioprostheses produced in accordance with the present disclosure can be used as replacements for defective tissues in mammals, particularly humans. Methods of effecting the replacement of, for example, heart valves, tendons, ligaments, vessels, etc., are well known in the art.

In some aspects, a tissue is substantially free of nucleic acids. In some aspects, a tissue is less than 90, 90, 91, 92, 93, 94, 95, 96, 97, 98, 99, or 100% free of nucleic acids. In some aspects the nucleic acid is RNA. In some aspects the nucleic acid is DNA. In some aspects, the tissue has less than 0.5 ng/mg (dry weight of tissue) of DNA. In some aspects, the tissue has less than 0.5 ng/mg (dry weight of tissue) of DNA as measured by a PicoGreen® DNA Assay.

In some aspects, a tissue is substantially free of one or more major histocompatibility molecules (MHC). In some aspects, a tissue is less than 90, 90, 91, 92, 93, 94, 95, 96, 97, 98, 99, or 100% free of one or more major histocompatibility molecules (MHC). In some aspects, the MHC is HLA-DR. In some aspects, the tissue is substantially free of HLA-DR as measured by immunohistochemistry. In some aspects, the MHC is HLA-A,B,C. In some aspects, the tissue is substantially free of HLA-A,B,C as measured by immunohistochemistry.

In some aspects, a tissue is substantially free of one or more microbes. In some aspects, a tissue is less than 90, 90, 91, 92, 93, 94, 95, 96, 97, 98, 99, or 100% free of one or more microbes. In some aspects, the one or more microbes include bacteria, viruses, and fungi. In some aspects, the one or more microbes is a bacteria. In some aspects the bacteria is a *Staphylococcus aureus* bacteria, a *Streptococcus pyogenes* bacteria, an *Enterococcus* bacteria, or a *Bacillus subtilis* bacteria. In some aspects the bacteria is a *Staphylococcus* bacteria, a *Streptococcus* bacteria, an *Enterococcus* bacteria, or a *Bacillus* bacteria. In some aspects, the presence or absence of *Bacillus* is an accepted surrogate for the presence or absence of *Clostridium* due its undesirable properties and higher risk. In some aspects, sterility of the tissue is achieved based upon meeting a 6 log 10 reduction in bacterial species according to known international standards. In some aspects, the tissue is substantially free of fungus.

In some aspects, a tissue is substantially free of one or more cellular components. In some aspects, a tissue is less than 50, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% free of one or more cellular components. In some aspects, the one or more cellular components include one or more cytoskeletal proteins. In some aspects, the one or more cytoskeletal proteins can include vimentin, beta-actin, alpha-actin, myosin, tubulin, and/or vinculin. In some aspects, the one or more cytoskeletal proteins include beta-actin. In some aspects, the tissue is substantially free of Beta-Actin as measured by immunohistochemistry. In some aspects, the one or more cytoskeletal proteins include vimentin. In some aspects, the tissue is substantially free of Vimentin as measured by immunohistochemistry.

In some aspects, the tissue comprises elastin. In some aspects, the tissue comprises elastin as measured by histology using Van Gieson stain. In some aspects, the tissue comprises one or more proteoglycans. In some aspects, the tissue comprises one or more proteoglycans as measured by histology using Masson's Trichrome stain.

In some aspects, the collagen structure of the tissue is not substantially altered compared to a fresh control tissue. In some aspects, the collagen structure of the tissue is not substantially altered compared to a fresh control tissue as assessed by the thermal stability of collagen. In some aspects, the denaturation temperature of the tissue is not substantially altered compared to a fresh control tissue. In some aspects, the denaturation temperature of the tissue is about 60, 60, 61, 62, 63, 64, 65, 66, 67, 68, 69, about 70, or 70° C. In some aspects, the denaturation temperature of the tissue is measured by a Hydrothermal Isometric Tension (HIT) test.

Kits

In some embodiments, the invention further provides kits comprising the tissues and/or compositions described herein. In some embodiments, the invention further provides kits comprising the tissues described herein. In some embodiments, a kit can include one or more of the solutions described herein. In some embodiments, a kit can include a hyptotonic solution, a first surfactant solution, a nuclease enzyme solution, a cleaning solution, and a bioburden reducing agent solution. In some embodiments, a kit can include an untreated tissue. In some embodiments, a kit can include instructions for decellularizing an untreated tissue. In some embodiments, a kit can include instructions for use one or more solutions described herein. In some embodiments, a kit can include instructions for treating an untreated tissue with one or more of the solutions described herein. In some embodiments, a kit can include instructions for using the solutions described herein in a method described herein.

In an embodiment, the invention provides a kit comprising a composition of the invention, e.g., a composition comprising decellularized tissue in a solution, in an appropriately labeled container. In certain embodiments, such kits comprise one or more individually labeled containers containing unit-dosage or multi-dosage aliquots of the composition, useful for administering a defined amount of the composition to an individual. The kit can additionally comprise instructions for administering the compositions of the invention to an individual, including, e.g., instructions on the manner of transplanting the tissue.

In an embodiment, the invention provides a kit comprising one or more solutions of the invention in an appropriately labeled container. In certain embodiments, such kits comprise one or more individually labeled containers containing unit-dosage or multi-dosage aliquots of the one or more solutions, useful for preparing a defined amount of the tissue for use in an individual. The kit can additionally comprise instructions for contacting a tissue with one or more of the solutions. In some embodiments, a kit can include instructions for carrying out one or more of the methods described herein, e.g., the methods described in the claims as filed.

The container in which kit components are handled and sold can be labeled per applicable Food and Drug Administration standards.

Although the foregoing methods, kits, and compositions have been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of these embodiments of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B(1992).

Example 1

Decellularization of Human Skin

Materials and Methods
Decellularization Protocol

Fresh frozen human skin from 6 donors (n=6) was procured, thawed at room temperature in its packaging, and prepared for treatment. The extent of tissue preparation was dependent upon the quality of the skin obtained, but generally involved removing extraneous tissue elements and cutting the tissue to size. The size of skin used was 4 cm×5 cm and tissues were treated with a minimum volume ratio of solution to tissue of 50:1 unless otherwise stated. For this example, three specimens of human skin were treated in one container. All chemicals were obtained from Sigma-Aldrich unless otherwise noted and the product numbers are provided in brackets.

The basic decellularization protocol followed is outlined in FIG. 1. This first stage of the decellularization treatment was designed to (i) cause the cells in the tissue to absorb water (hypotonic conditions) and eventually burst and (ii) cause the intact epidermal layer to separate from the underlying dermis while leaving the basement membrane intact. Specimens of fresh human skin were transferred to a lidded polypropylene jar containing 300 mL of a hypotonic solution containing 10 mM Tris buffer (Trizma Base, T87602) and 5 mM ethylenediaminetetraacetic acid (EDTA, E9884) as a metalloprotease inhibitor. This solution was adjusted to pH=8 using HCl/NaOH prior to use. To this container was added 5 mL/L of a penicillin/streptomycin 100× solution (A5955, stock concentration of 10,000 U/mL/10,000 mg/mL) and 0.35 mL/L of a stock solution (5% w/v in 100% ethanol) of the serine protease inhibitor phenylmethanesulfonyl fluoride (PMSF, P7626). The container was then allowed to mix gently on a shaker table at 40-65 RPM, T=20-25° C., for 24 hours with fresh solution changed at 12 hours. During the first 12 hours of treatment, the epidermis of the skin samples was released from the underlying dermis and was removed from the container when the solution was refreshed.

This next stage of the treatment was designed to remove cell membranes and cytoskeletal components. The hypotonic solution was decanted and replaced with 300 mL of a high saline solution containing 5 M potassium chloride (KCl, P9541), 50 mM Tris buffer (T87602) containing 1% (v/v) Triton X-100 (octyl phenoxy polyethoxyethanol, T9284), and a metalloprotease inhibitor (5 mM of EDTA, E9884). This solution was adjusted to pH=8 using HCl/NaOH prior to use. To this container was added 5 mL/L of a penicillin/streptomycin 100× solution (A5955, stock concentration of 10,000 U/mL/10,000 mg/mL) and 0.35 mL/L of a stock solution (5% w/v in 100% ethanol) of the serine protease inhibitor phenylmethanesulfonyl fluoride (PMSF, P7626). The container was allowed to mix gently on a shaker table (at 40-65 RPM), T=20-25° C., for 36 hours with fresh solution changed every 12 hours.

To ensure sterility, all work from this point onward was carried out in a Class II/III biological safety cabinet using aseptic technique. The previous high saline solution was decanted and replaced with 300 mL of sterile, deionized water. Specimens were rinsed for 30 minutes. Following the rinse, the sterile deionized water was decanted and replaced with 300 mL of sterile Hanks'/HEPES physiological buffer (0.14 M Sodium Chloride (S9625), 5.4 mM Potassium Chloride (P9541), 0.26 mM Sodium Phosphate dibasic (S0876), 0.44 mM Potassium Phosphate monobasic (P5379), 4.2 mM Sodium Bicarbonate (S8875), 10 mM HEPES Sodium salt (H7006), 8.3 mM Calcium Chloride dihydrate (C3881), 0.2 mM Magnesium Sulfate heptahydrate (M1880), and 0.25 mM Magnesium Chloride hexahydrate (M0250). This solution was adjusted to pH 7.35 using HCl/NaOH prior to use. Specimens were rinsed in the Hanks'/HEPES physiological buffer for 30 minutes.

The next stage of the process is designed to degrade DNA and RNA to facilitate their subsequent removal. The Hanks'/HEPES physiological buffer used for the rinse was decanted and replaced with 200 mL of Hanks'/HEPES physiological buffer containing 1330 μL of deoxyribonuclease stock solution (DNAse type II from bovine pancreas (D4527)), 13.3 U/μL, in a 0.175 g NaCl (S9625)/10 mL glycerol (G7757)/10 mL sterile water solution adjusted to pH 7.3) and 1330 μL of ribonuclease stock solution (RNAse type III-A from bovine pancreas (R5125), 85 μg/mL, in a 0.03 g Trizma Base (T87602)/0.22 g NaCl (S9625)/25 mL sterile water solution adjusted to pH 7.5). The tissue was then placed in a shaking water bath, gently mixed (45-60 RPM) at 37° C. for 5 hours. After 5 hours the solution was decanted and replaced with fresh, sterile Hanks'/HEPES physiological buffer, briefly rinsing the tissue.

The next stage of the process was designed to further remove any remaining cellular components (cytoskeletal proteins, DNA, RNA) as TnBP is a "surfactant like" chaotropic solvent. The previous physiological buffer rinse was decanted and replaced by 300 mL of either (i) a 50 mM Tris buffer (Trizma Base, T87602) solution in water adjusted to pH 9 and containing 1% (v/v) Tri-n-butyl phosphate (TnBP, 158615), 5 mL/L of a penicillin/streptomycin antibiotic/antimycotic 100× solution (stock concentration of 10,000 U/mL/10,000 mg/mL) with samples denoted as "Aqueous Decellularization" or (ii) a 50 mM Tris buffer (Trizma Base, T87602) solution in 70% Ethanol adjusted to pH 9 and containing 1% (v/v) Tri-n-butyl phosphate (TnBP, 158615) with samples denoted as "Ethanol Decellularization." The samples of tissue were then gently mixed on a shaker table (45-60 RPM) at T=20-25° C. for 48 hours with fresh solution changes every 12 hours.

After treatment, the solutions were decanted and refreshed with 300 mL of 50 mM Tris buffer (Trizma Base, T87602) solution, adjusted to pH 9 and containing 5 mL/L of a penicillin/streptomycin antibiotic/antimycotic 100× solution (stock concentration of 10,000 U/mL/10,000 mg/mL). The container was then allowed to mix gently on a shaker table (at 40-65 RPM), T=20-25° C., for 24 hours with fresh solution changed at 12 hours.

Next, the previous pH 9 Tris buffer solution was decanted and replaced with fresh, sterile, phosphate-buffered saline solution (PBS) containing 0.14 M sodium chloride (NaCl, S9625), 2.7 mM potassium chloride (KCl, P9541), 6.5 mM sodium phosphate dibasic (S0876), 1.5 mM potassium phosphate monobasic (P5379), adjusted to pH 7.4, and containing 5 mL/L of a penicillin/streptomycin antibiotic/antimycotic 100× solution (stock concentration of 10,000 U/mL/10,000 mg/mL). The container was allowed to mix gently on a shaker table (at 40-65 RPM), T=20-25° C., for 12 hours. After, the tissue specimens were rinsed twice (30 minutes each) with 300 mL of fresh sterile phosphate buffered saline solution containing no antibiotics/antimycotics.

In a final step, each piece of tissue was bottled under sterile conditions in 100 ml of fresh sterile phosphate buffered saline (PBS) solution infused with penicillin/streptomycin (6 mL/L of 100× solution with a stock concentration of 10,000 U/mL/10,000 mg/mL), labeled as either "Aqueous Decellularization" or "Ethanol Decellularization" and stored at 4° C. until used for histological, immunohistochemical, DNA content, and Hydrothermal Isometric Tension (HIT) analyses as outlined below.

Histology

Histology samples were prepared from the central portion of each piece of human skin (Fresh, Aqueous Decellularization, Ethanol Decellularization). Samples were placed in 10% acetate buffered formalin (Sigma-Aldrich, HT50-1-128) for 48 hours, after which they were transferred to 100% ethanol in preparation for paraffin embedding. After embedding, samples were sectioned using a microtome, with section thickness set at 5 μm. Sections were mounted on silinated glass slides and dried for a minimum of two hours. After drying, slides were subjected to a series of wash and staining steps using protocols for Hematoxylin and Eosin (stains cell nuclei blue and collagen pink), Masson's Trichrome (stains cell nuclei blue/black, collagen and proteoglycans blue/green), and Verhoff-Van Gieson (stains cell nuclei black, collagen red/pink, elastin fibres black). After these steps, sections were sealed and covered using glass coverslips. For each sample, two sections were evaluated along their entire length under 10×, 20× and 40× objectives, a thorough description of each slide was recorded and representative images captured with a digital camera. Decellularized human skin prepared using Aqueous Decellularization and Ethanol Decellularization were compared to untreated Fresh human skin (control).

Immunohistochemistry

Formalin-fixed, paraffin-mounted tissue sections (5 μm thickness) were prepared and dewaxed using xylenes and ethanol. Slides were washed in phosphate buffered saline (PBS), and antigen retrieval was carried out using a citrate buffer (pH=6.1) and pressure cooker (HEIR). After antigen retrieval, samples were then placed in 2% hydrogen peroxide in PBS for 10 minutes for blocking of endogenous peroxidases. After a brief PBS wash, samples were blocked with Protein Block (Dako, X0909) for 10 minutes in a humid chamber. Primary antibody (25 μL) was placed on each sample and incubated for 18 hours in a humid chamber. Primary antibodies included anti-vimentin (Dako, M7020, dilutions of 1:40, 1:80), anti-Beta Actin (Sigma, A5316, dilutions of 1:2000, 1:4000), anti-HLA-DR (Dako, M0746, dilutions of 1:50, 1:100), and anti-HLA-A,B,C (Abcam, ab70328, dilutions of 1:200, 1:400). After incubation, samples were washed in PBS, and treated using a Universal LSAB+Kit/HRP (Dako, K0690) for rabbit/goat/mouse antibodies according to manufacturer's instructions. Samples were washed with PBS, and color was developed using DAB+Chromogen+substrate buffer for 7 minutes. After a brief water wash, samples were counterstained using Mayer's Hematoxylin for 2 minutes, Scott's water for 2 minutes.

Samples were then dehydrated (xylenes and ethanol) and mounted with cytoseal and glass coverslips. For each sample, two sections were evaluated along their entire length under 10×, 20× and 40× objectives; a thorough description of each slide was recorded. Representative images at 20× and 40× and a complete scan of one section at 10× were captured with a digital camera. A composite of the complete scan of a section was created by piecing together individual images captured along the sample using the 10× objective. Decellularized human skin prepared using Aqueous Decellularization and Ethanol Decellularization was compared to untreated Fresh human skin. Negative controls included sections treated by omitting primary or secondary antibodies.

DNA Quantification

The quantity of DNA present in Fresh human skin, Aqueous Decellularized, and Ethanol Decellularized treated human skin was determined using a fluorescence-based assay. Representative tissue samples from each treatment condition were freeze-dried and weighed prior to the assay. To disassociate the DNA from the tissue, a small piece of freeze-dried tissue (9-11 mg dry weight (wt)) from each sample was digested by papain. Papain digest solution was made by preparing buffer solution (50 ml of digestion buffer was prepared by combining 0.130 g ammonium acetate (Sigma-Aldrich, A1542), 0.019 g $Na_2EDTA.2H_2O$ (Sigma-Aldrich, E5134) and 0.015 g. DL-dithiothreitol (DTT) (Sigma-Aldrich, 43815) in distilled water with pH adjusted to 6.2 and adding lyophilized papain (Sigma-Aldrich, P4762) to a concentration of 1 mg/mL. Digest solution was added to each sample at a ratio of 100 4 per mg dry weight to normalize the quantity of tissue per volume. Following digestion, each sample was briefly centrifuged at 10,000 g to remove insoluble or undigested material. A small aliquot (50 µL) from each digested sample was analyzed using the Quant-iT Picorgreen Assay Kit (Invitrogen, P7581) according to the manufacturer's instructions. Standard curves were created in the range of 0-1,000 ng/ml for Fresh skin and 0-12.5 ng/ml for Aqueous Decellularized and Ethanol Decellularized skin. The fluorescence was measured on a multiplate reader at an excitation wavelength of 485 nm and an emission wavelength of 528 nm. All readings were performed in duplicate and in black 96-well plates to prevent 'cross-talk' between the wells. Results were normalized to the dry weight of tissue analyzed for each sample.

Hydrothermal Isometric Temperature (HIT) Test

Samples were tested in a custom-built, multisample HIT apparatus, as described by Lee et al. [Lee et al. (1995)]. Samples were tested in groups, up to six at a time. Stainless steel spring clamps were used to grip samples (n=4) of Fresh, Aqueous Decellularized, and Ethanol Decellularized skin (≈2.5 cm×0.5 cm), leaving ≈10 cm of tissue between the grips. An initial load of 50 g (0.5 N) was applied to each of the samples, suspended in a 4-liter beaker containing distilled water. The samples were then heated at a rate of ≈1-2° C./min from room temperature to an isotherm maximum temperature of 90° C. Temperatures were measured using a centrally located thermistor probe positioned at midsample height. Load data were acquired using custom-built straingauged cantilever load cells. The load cells and temperature probe were interfaced with a conditioning amplifier, and both data acquisition and system control were accomplished via a personal computer equipped with a 12-bit A/D, D/A DAQ board (Model NB-MIO-16L; National Instruments) and custom-written software programmed using LabVIEW 7.1 software (National Instruments). Temperature-time-load data were generated throughout HIT testing. As the water in which the samples were immersed was heated from ambient temperature to the 90° C. maximum, load, temperature, and time data were captured in 1° C. intervals. A key measure of collagen's hydrothermal stability is the temperature at which a triple helix denatures, its denaturation temperature (Td). This is the temperature at which enough thermal energy has been transferred to the sample to overcome the energy barrier to uncoiling and allow change to a new, lower-energy conformation. In HIT testing, samples are held under isometric constraint such, that when enough thermal energy is added, the collagen molecules within the sample become able to uncoil. Their actual uncoiling is prevented as the sample is being held under isometric constraint and the energetic impetus to uncoil generates a tensile force that is recorded as a distinctive increase in the load on the sample. This creates an elbow in the load-temperature plot and the temperature at which this elbow begins is termed the Td of the sample. Different regions within a collagenous sample, and within an individual collagen molecule for that matter, have varying degrees of thermal stability. The Td value recorded in this work therefore is a function of the thermal stability of all of the load-bearing collagen in the sample during testing.

Statistics for HIT

Comparisons made between groups were conducted using a one-way ANOVA and the Tukey-Kramer HSD test. Comparisons were made at 95% significance ($\alpha=0.05$). Note that the resolution of the HIT test is 1° C. and that changes in Td from control (fresh) tissue of greater than or equal to 3° C. is deemed practically significant.

Results

Histology

Figure 2:
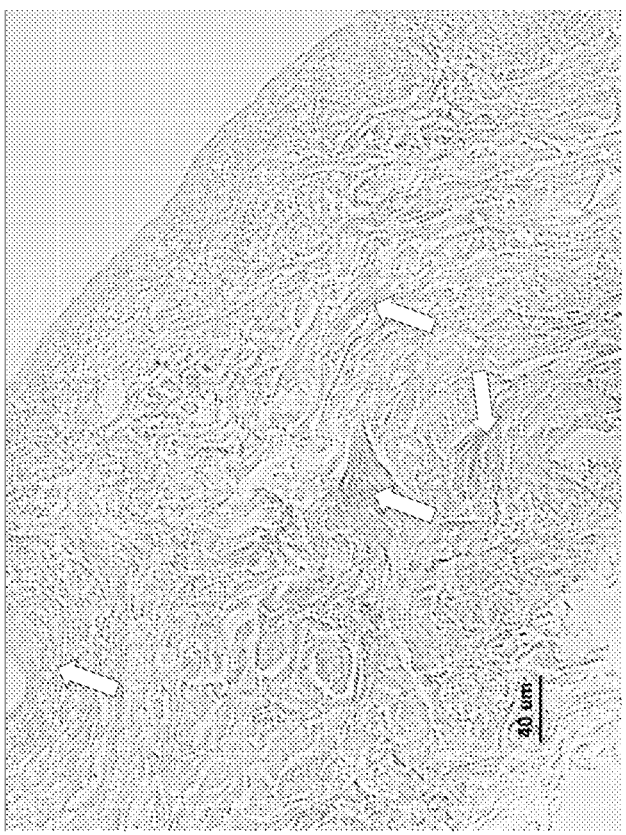
FIG. 2. Histology of the fresh (left) and decellularized (right) human skin allograft. Note preservation of collagen fibre matrix (pink; examples shown with white arrows) and complete lack of cell nuclei (blue; examples shown with black arrows) after decellularization. Hematoxylin and Eosin stain, 200×.
Figure 2:
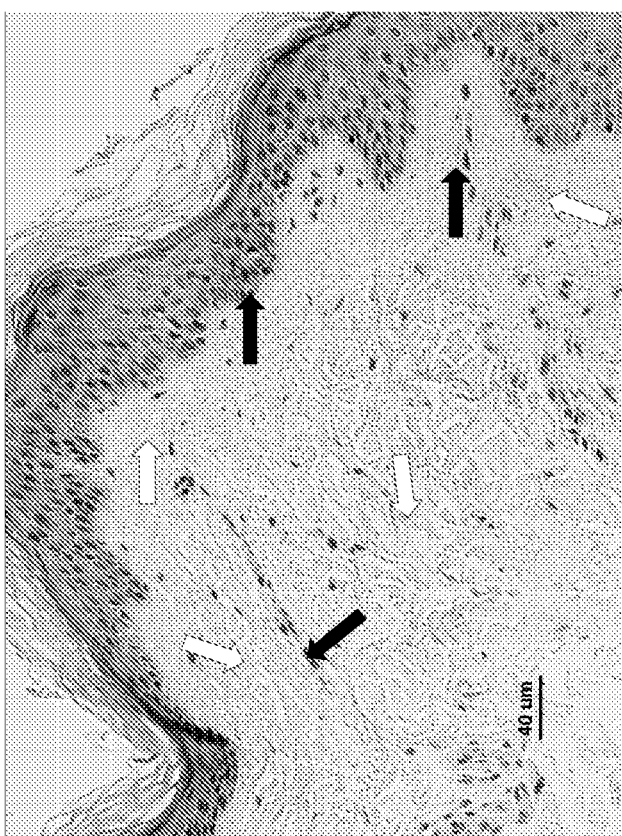

Sections of fresh human skin stained with hematoxyin and eosin revealed dense packing of cell nuclei (dark blue) in the epidermis below the keratinized layer and individual and clusters of cell nuclei throughout the dermis (FIG. 2). After decellularization by both Aqueous and Ethanol Decellularization techniques, there was a complete absence of any staining for cell nuclei as observed under 100×, 200× and 400× magnifications (FIG. 2). Collagen structure, stained pink by eosin, however, appeared well-preserved in all decellularized skin.

Figure 3:
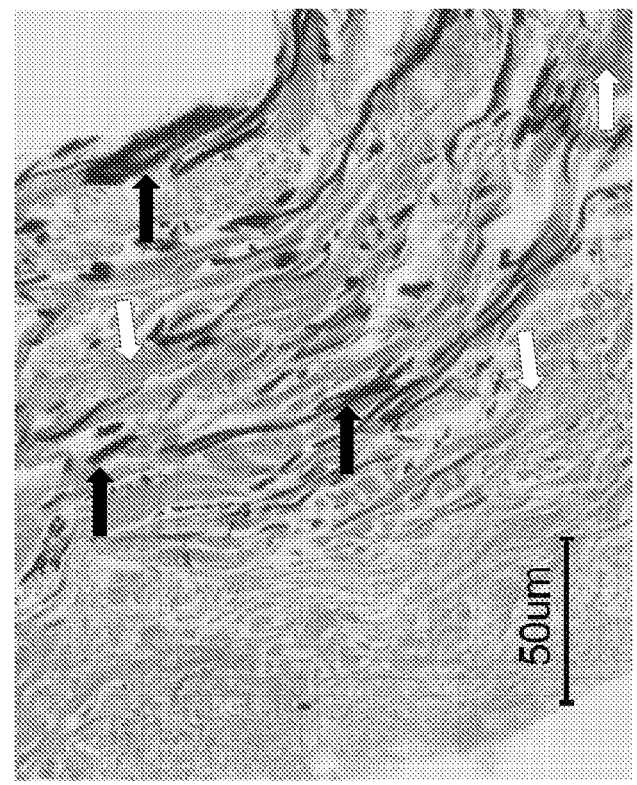
FIG. 3. Histology of the fresh (left) and decellularized (right) human skin allograft. Note preservation of collagen (pink; examples shown with white arrows) and elastin (black; examples shown with black arrows) fibre matrix. Verhoeff—Van Gieson stain, 400×.
Figure 3:
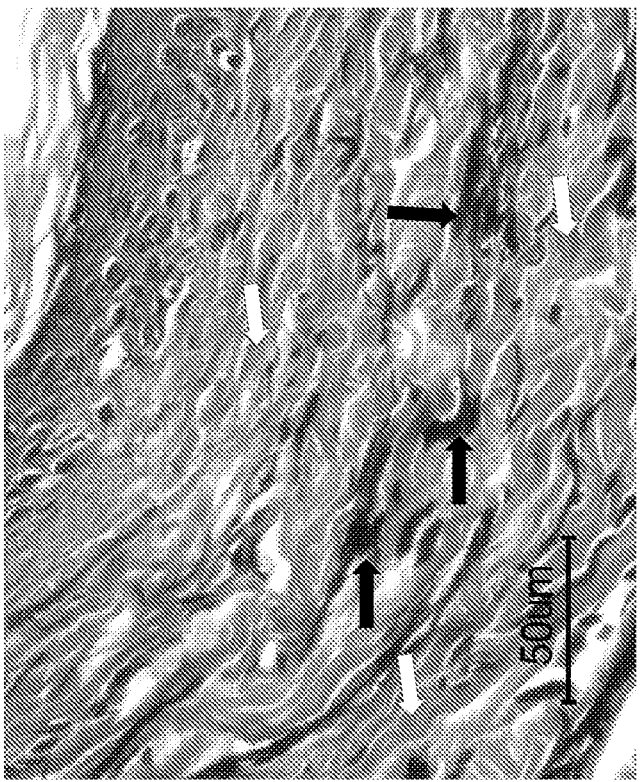

Fresh human skin sections stained with Verhoff-Van Gieson stain revealed numerous black cell nuclei in the non-keratinized epidermis, strong black staining elastic fibres within the deeper dermis, and pink collagen matrix in the dermis (FIG. 3). After decellularization by all methods, the cells in the epidermis were no longer visible, however the relative intensity of both the collagen (pink) and elastin fibres (black) in the dermis were similar to that of fresh skin (FIG. 3).

Figure 4:
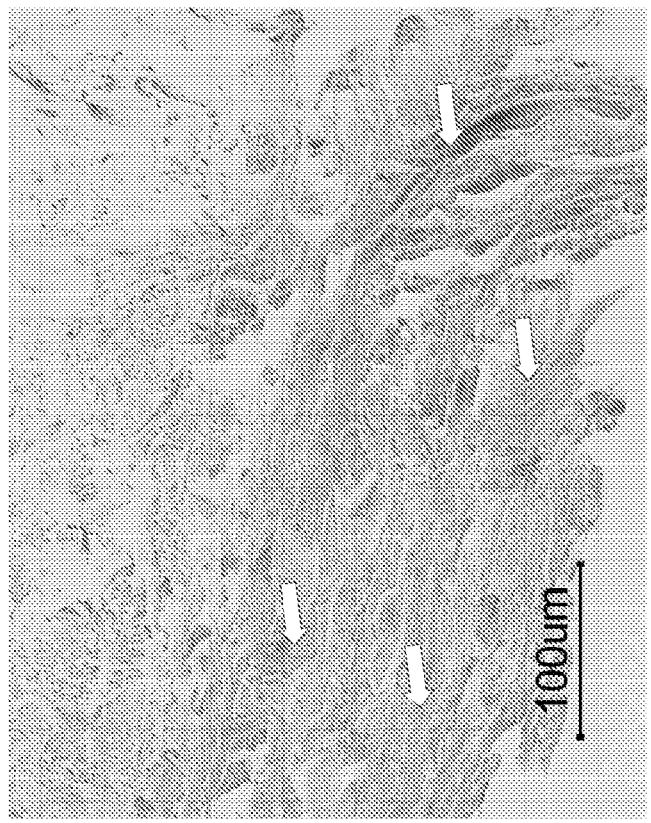
FIG. 4. Histology of the fresh (left) and decellularized (right) human skin allograft. Tissue sections from fresh human skin (on the left) stained with Masson's Trichrome stain (stains cells nuclei (blue; examples shown with grey arrows), cell cytoplasm (red/purple; examples shown with black arrows) and collagen, elastin and proteoglycans of the extracellular matrix (green; examples shown with white arrows) reveal the presence of numerous cells in both the epidermis (bottom of micrograph) and dermis (middle and top of micrograph) with intact collagen, elastin, and proteoglycans. In contrast, after decellularization (on the right), only green staining remains indicating the presence of collagen, elastin, and proteoglycans in the absence of cellular materials. Masson's Trichrome stain, 200×.
Figure 4:
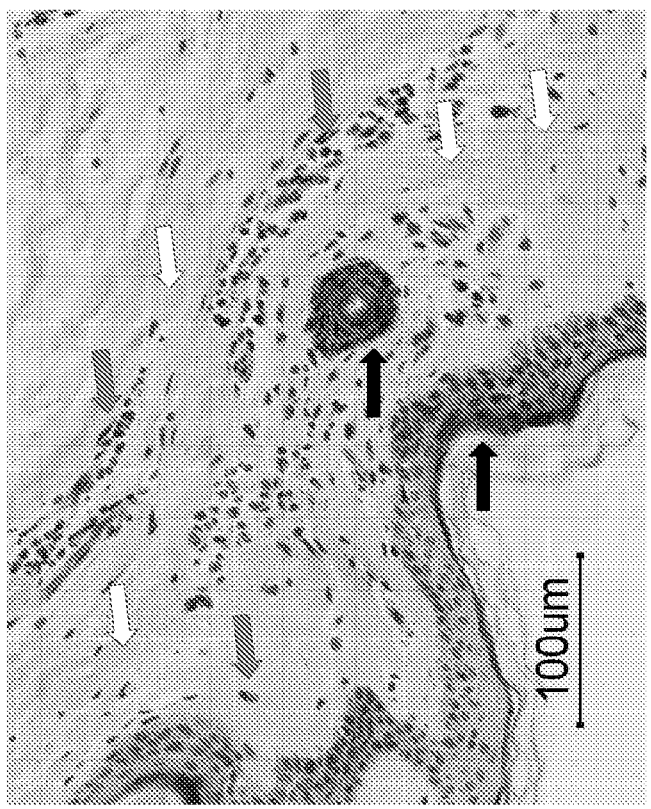

Masson's Trichrome staining of fresh human skin revealed the presence of numerous blue stained cell nuclei and red stained cell cytoplasm in the epidermis and dermis. Features such as blood vessels and residual hair follicles could be observed. The dermis included blue/green stained collagen, elastin, and glycosaminoglycans (FIG. 4). After decellularization by all treatments, no evidence of dark blue or red staining indicating the presence of cells was present. Green staining, however, indicating the presence of collagen, elastin and glycosaminoglycans was evident (FIG. 4).

Immunohistochemistry

Figure 5:
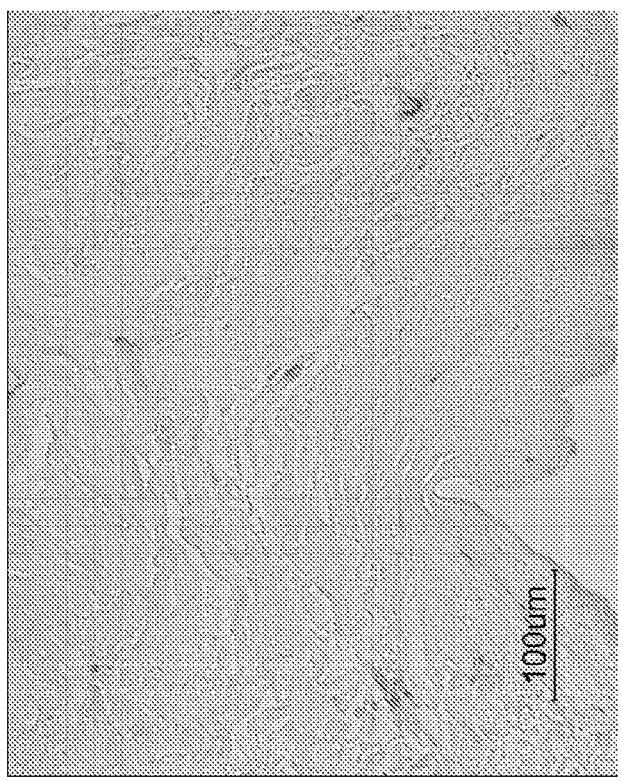
FIG. 5. Immunohistochemistry of fresh (left) and decellularized (right) human skin allograft for detection of cytoskeletal protein Vimentin. Tissue sections from fresh human skin (on the left) treated using a monoclonal antibody that specifically recognizes the cytoskeletal protein Vimentin and peroxidase as a stain, shows the presence of Vimentin in cells indicated by the dark brown colorations (examples shown with white arrows). In contrast, after decellularization (on the right), there was a substantial reduction in the amount and intensity of dark brown staining indicating the removal of the cell cytoskeletal protein Vimentin. Large areas devoid of any staining were seen within decellularized skin and where staining was evident, the intensity and frequency typically present is represented in the example shown on the right. Anti-Vimentin antibody, Peroxidase staining, 200×.
Figure 5:
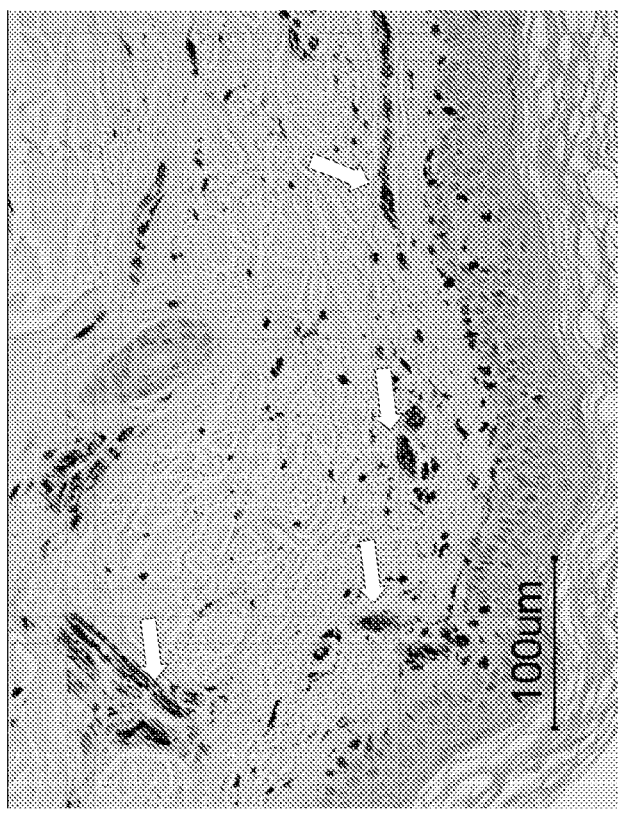
Figure 7:
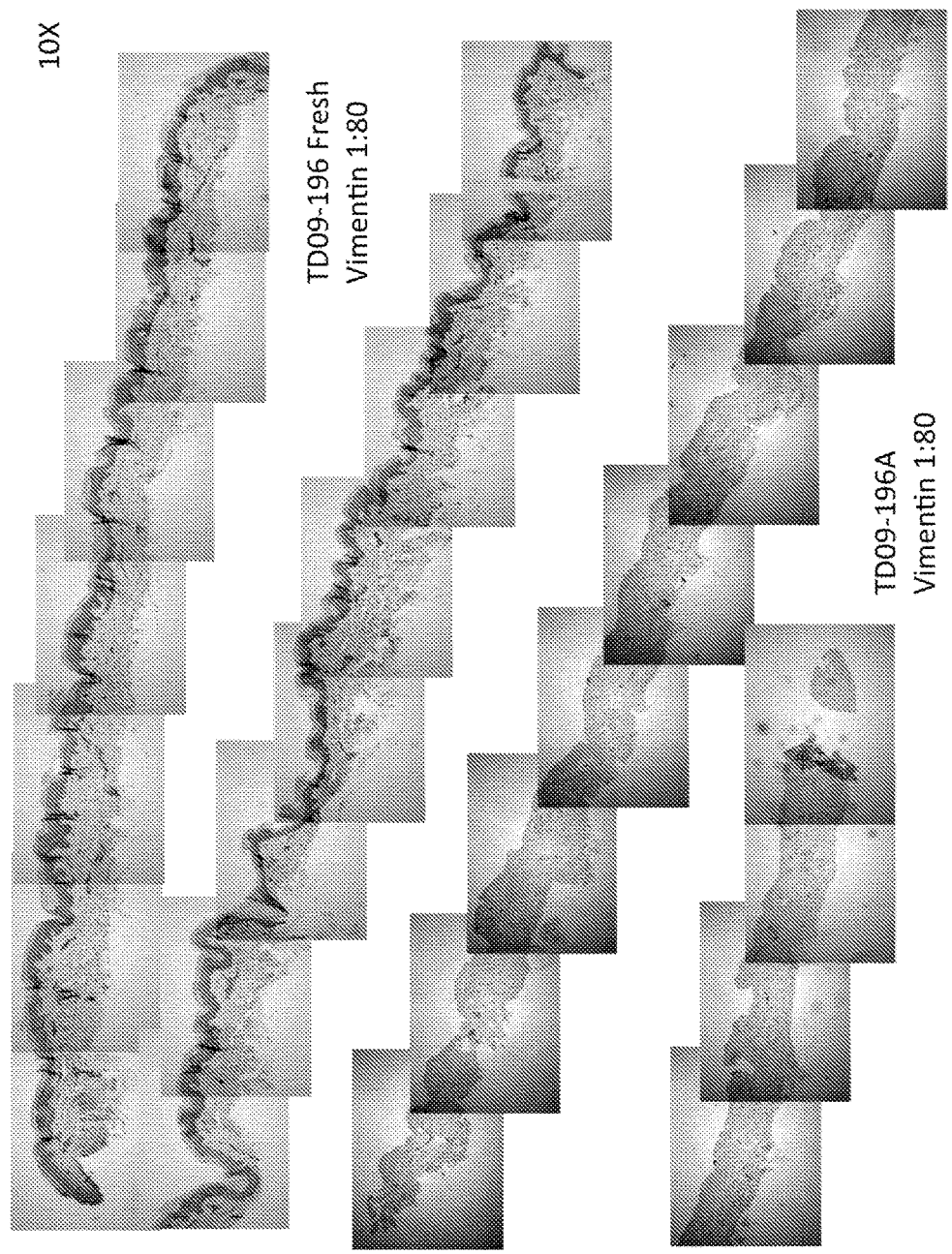
FIG. 7. Composite images of Fresh (top) and Aqueous Decellularized (bottom) human skin stained for the cytoskeletal protein vimentin (1:80 dilution) identified by dark grey/black coloration. The composite images were created from individual images taken at 100× magnification. The composite reveals the very sparse and minimal staining after decellularization indicating substantial removal of the cytoskeletal protein vimentin.
Figure 8:
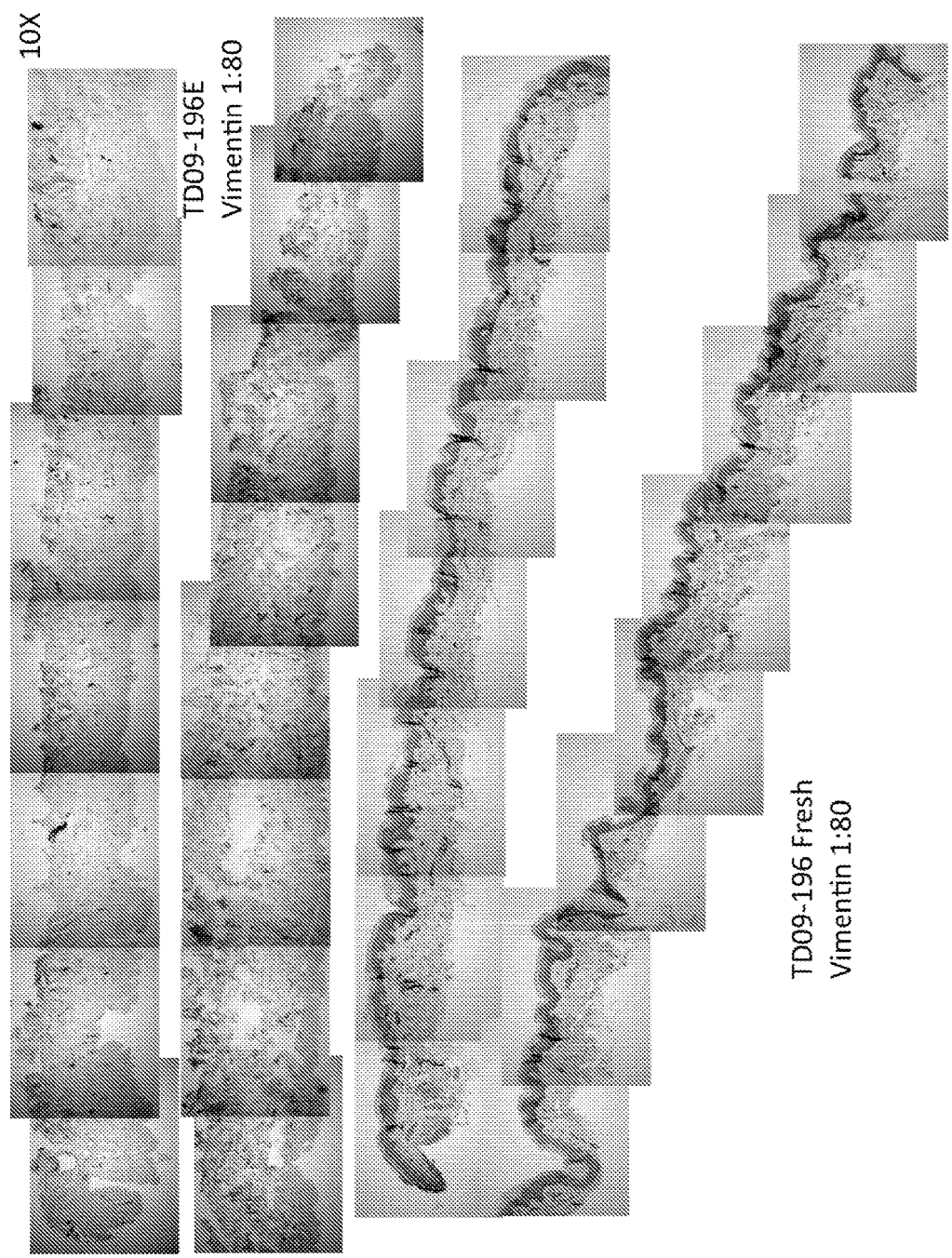
FIG. 8. Composite images of Fresh (bottom) and Ethanol Decellularized (top) human skin stained for the cytoskeletal protein vimentin (1:80 dilution) identified by dark grey/black coloration. The composite images were created from individual images taken at 100× magnification. The composite reveals the very sparse and minimal staining after decellularization indicating substantial removal of the cytoskeletal protein vimentin.

Staining of Fresh human skin for the cytoskeletal protein vimentin using monoclonal antibodies and peroxidase revealed positive stained cells as individuals and clusters throughout the tissue (FIGS. 5, 7 and 8). After decellularization by Aqueous or Ethanol Decellularization protocols, both the amount and intensity of positive staining for vimentin was significantly reduced (FIGS. 5, 7 and 8). Large regions devoid of any positive staining for vimentin were present. Composite images of complete sections of human skin before and after decellularization created by taking overlapping images at 100× magnification give a sense of the overall level of removal of vimentin (FIGS. 7 and 8).

Figure 6:
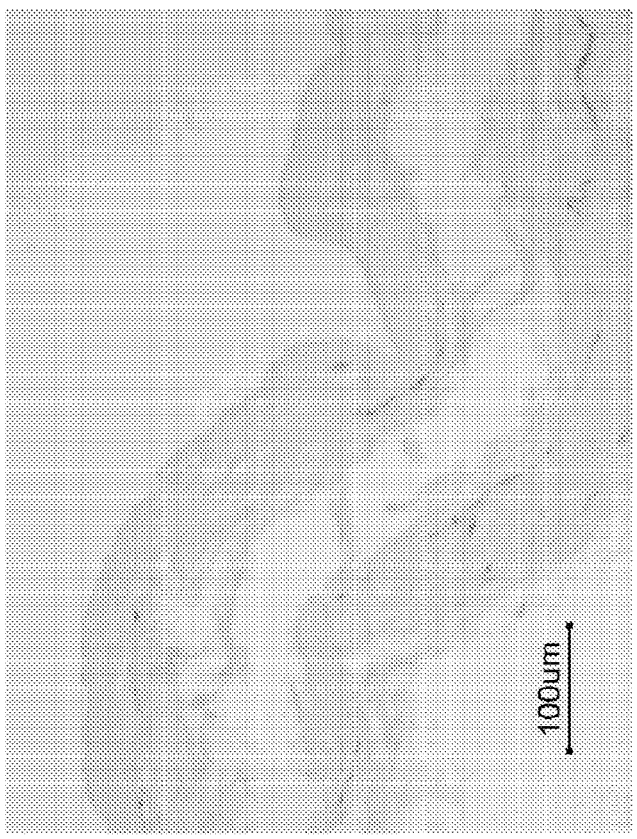
FIG. 6. Immunohistochemistry of fresh (left) and decellularized (right) human skin allograft for detection of cytoskeletal protein Beta-Actin. Tissue sections from fresh human skin (on the left) treated using a monoclonal antibody that specifically recognizes the cytoskeletal protein Beta-Actin and peroxidase as a stain, shows the presence of Beta-Actin in cells indicated by the dark brown colorations (examples shown with white arrows). In contrast, after decellularization (on the right), there was a substantial reduction in the amount and intensity of dark brown staining indicating the removal of the cell cytoskeletal protein Beta-Actin. Large areas devoid of any staining were seen within decellularized skin and where staining was evident, the intensity and frequency typically present is represented in the example shown on the right. Anti-Beta-Actin antibody, Peroxidase staining, 100×.
Figure 6:
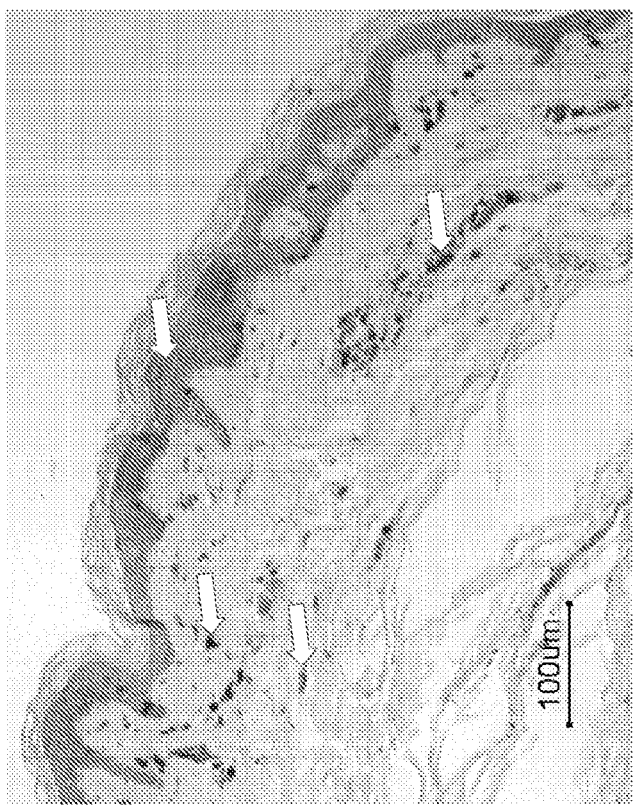
Figure 9:
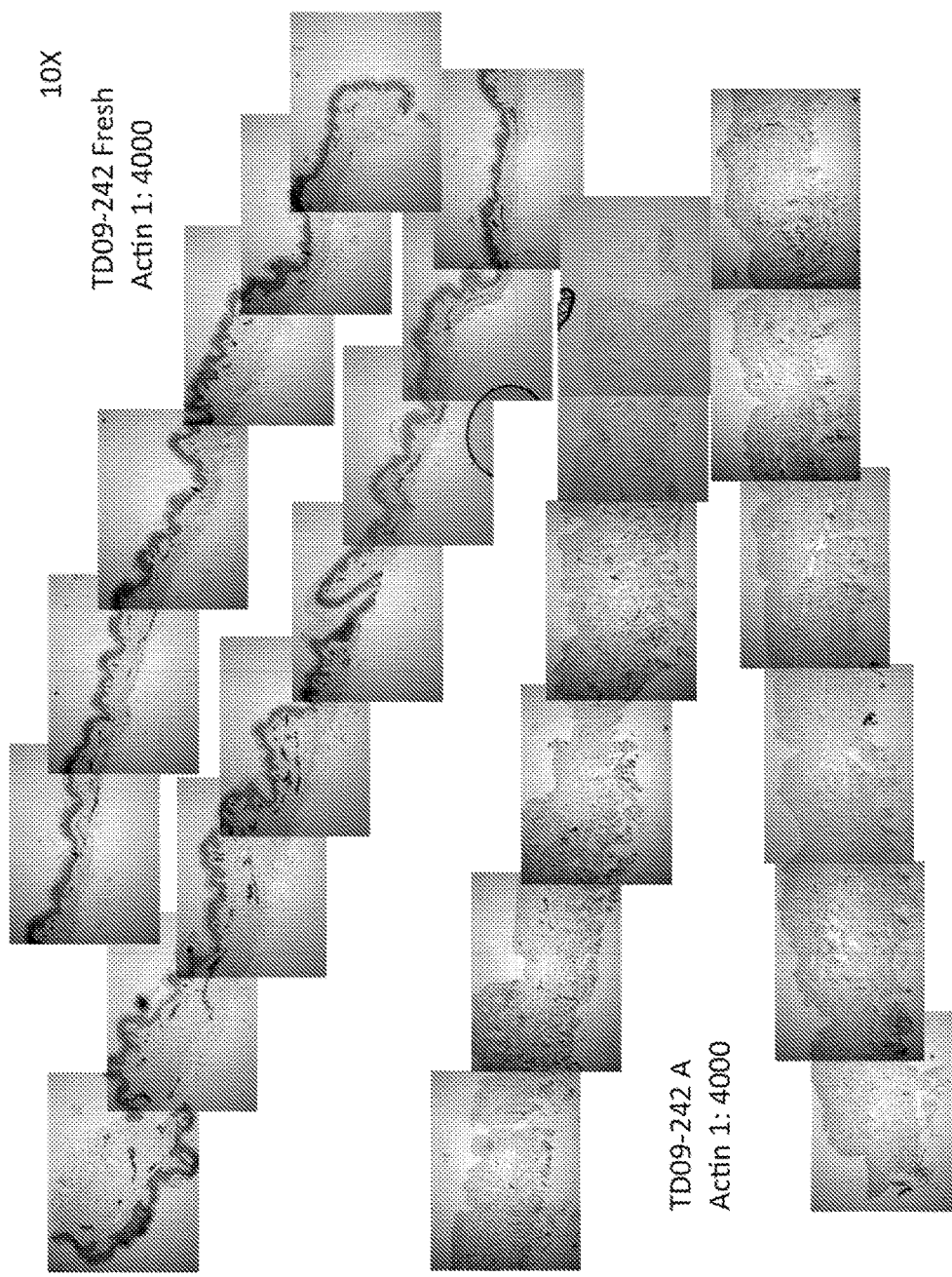
FIG. 9. Composite images of Fresh (top) and Aqueous Decellularized (bottom) human skin stained for the cytoskeletal protein Beta-actin (1:4000 dilution) identified by dark grey/black coloration. The composite images were created from individual images taken at 100× magnification. The composite reveals the very sparse and minimal staining after decellularization indicating substantial removal of the cytoskeletal protein Beta-actin.
Figure 10:
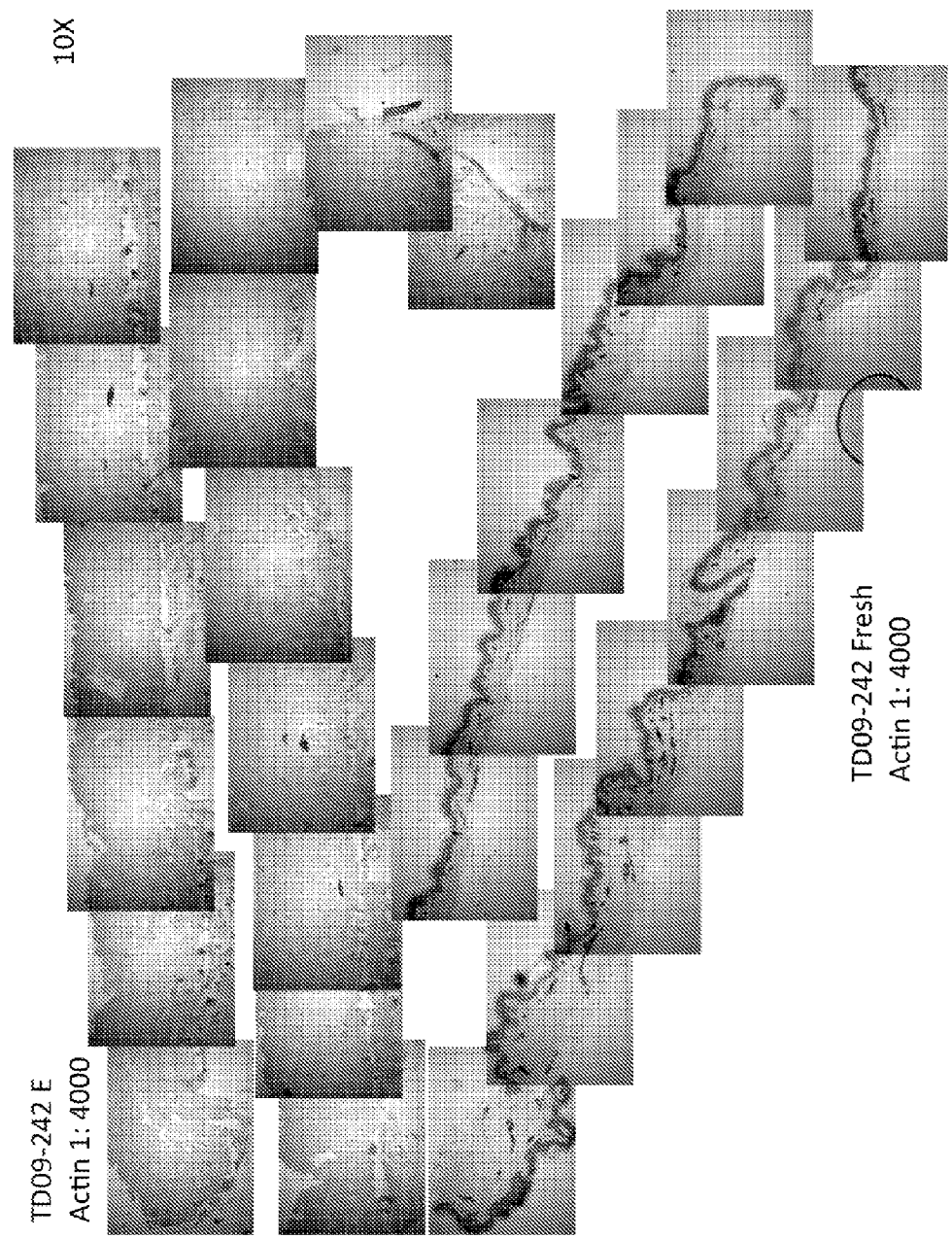
FIG. 10. Composite images of Fresh (bottom) and Ethanol Decellularized (top) human skin stained for the cytoskeletal protein Beta-actin (1:4000 dilution) identified by dark grey/black coloration. The composite images were created from individual images taken at 100× magnification. The composite reveals the very sparse and minimal staining after decellularization indicating substantial removal of the cytoskeletal protein Beta-actin.

Fresh human skin stained using antibodies against the cytoskeletal protein Beta-actin revealed strong positive staining throughout the non-keratinized epidermis and strong positive staining of individual and clusters of cells throughout the dermis (FIGS. 6, 9 and 10). After decellularization by Aqueous or Ethanol Decellularization protocols, both the amount and intensity of positive staining for Beta-actin was substantially reduced (FIGS. 5, 7 and 8). Large regions devoid of any positive staining for Beta-actin were present. Composite images of complete sections of human skin before and after decellularization created by taking overlapping images at 100× magnification give a sense of the overall level of removal of Beta-actin (FIGS. 7 and 8).

Figure 11:
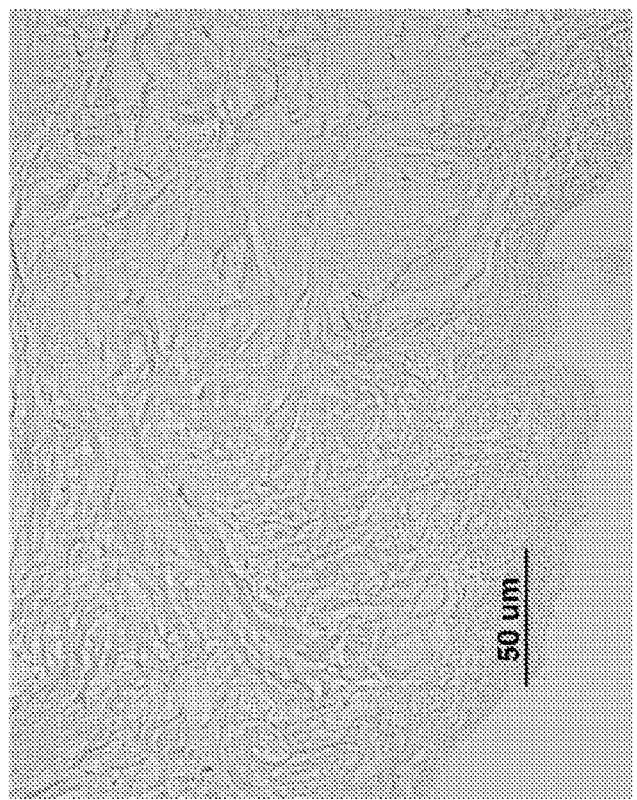
FIG. 11. Immunohistochemistry of fresh (left) and decellularized (right) human skin allograft for detection of Human Leukocyte Antigen HLA-A,B,C. Tissue sections from fresh human skin (on the left) treated using a monoclonal antibody that specifically recognizes the cell membrane protein HLA-A,B,C and peroxidase as a stain, shows the presence of HLA-A,B,C on cells indicated by the dark brown colorations (examples shown with white arrows). In contrast, after decellularization (on the right), there is an absence of dark brown staining indicating the removal of the HLA-A,B,C cell membrane protein. This is a direct indicator of the treatment's ability to remove cell membrane materials. Anti-HLA-A,B,C antibody, Peroxidase staining, 400×.
Figure 11:
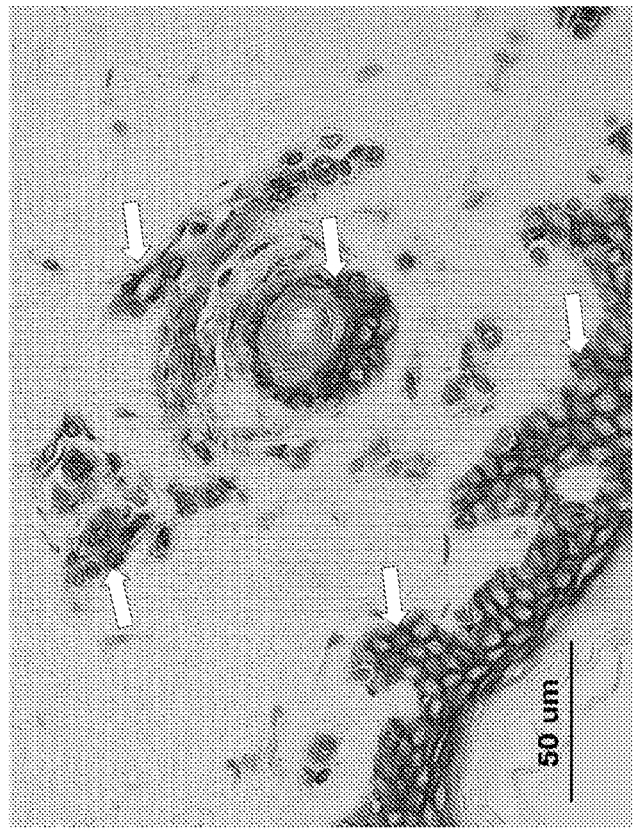
Figure 12:
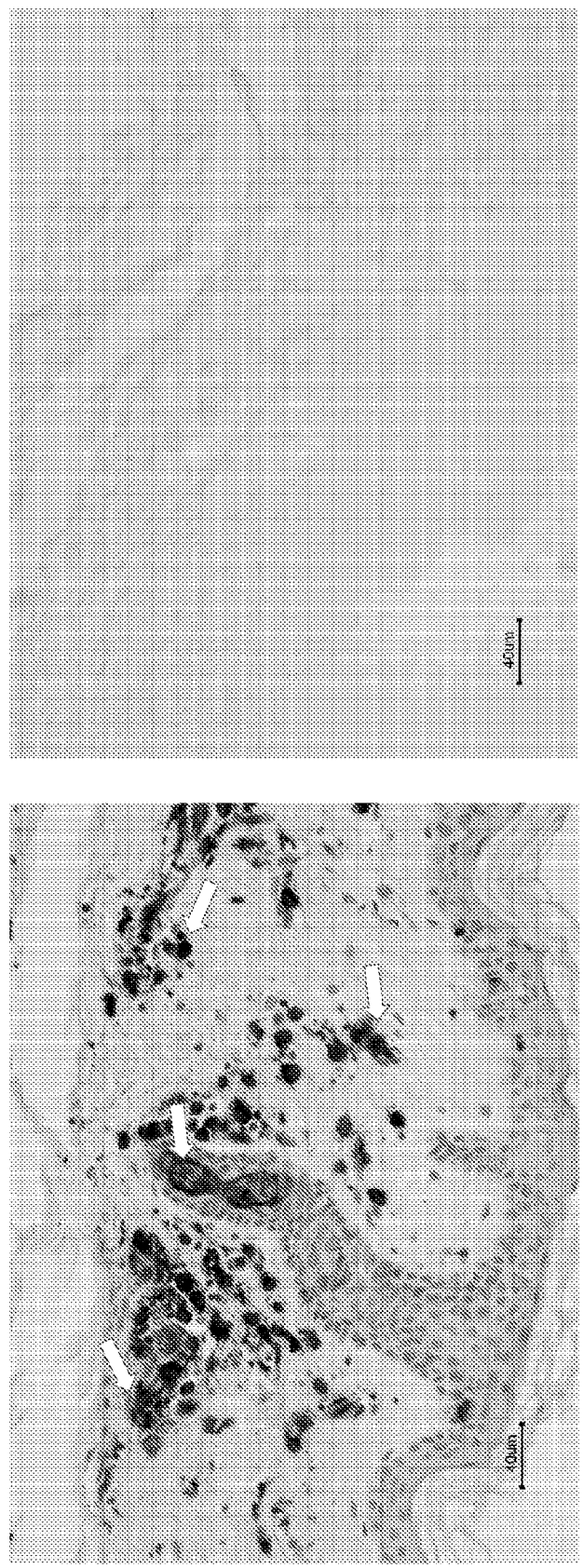
FIG. 12. Immunohistochemistry of fresh (left) and decellularized (right) human skin allograft for detection of Human Leukocyte Antigen HLA-DR. Tissue sections from fresh human skin (on the left) treated using a monoclonal antibody that specifically recognizes the immunogenic cell membrane protein HLA-DR and peroxidase as a stain, shows the presence of HLA-DR on cells indicated by the dark brown colorations (examples shown with white arrows). In contrast, after decellularization (on the right), there is an absence of dark brown staining indicating the removal of the immunogenic HLA-DR cell membrane protein. This is a direct indicator of the treatment's ability to remove cell membrane materials and a major protein associated with allograft rejection Anti-HLA-DR antibody, Peroxidase staining, 200×.
Figure 13:
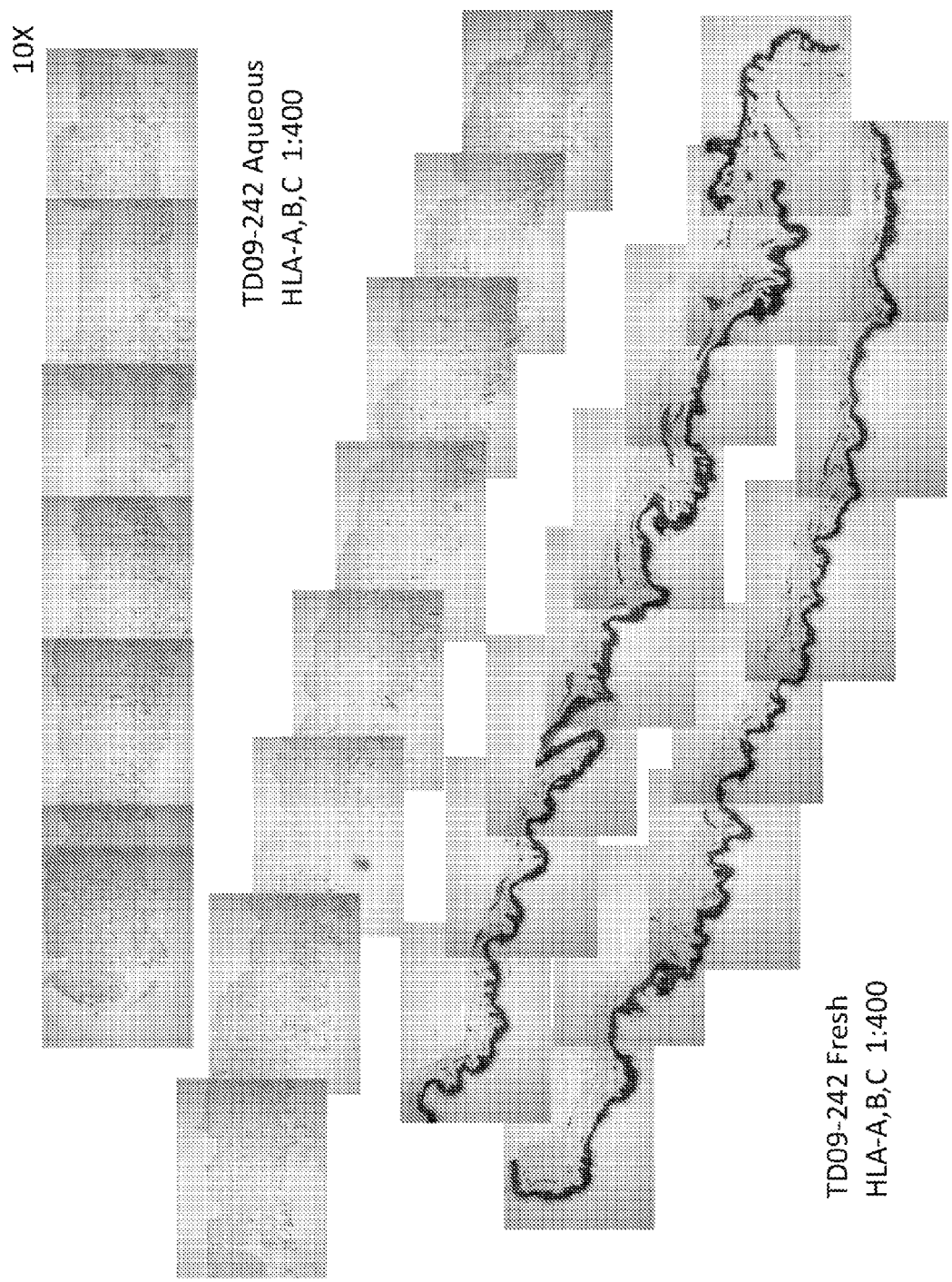
FIG. 13. Composite images of Fresh (bottom) and Aqueous Decellularized (top) human skin stained using a monoclonal antibody (1:400 dilution) that specifically recognizes the cell membrane protein HLA-A,B,C and peroxidase as a stain. The presence of HLA-A,B,C on cells is indicated by the dark grey/black coloration. In contrast, after decellularization (on the top), there is an absence of staining indicating the removal of the HLA-A,B,C cell membrane protein. The composite images were created from individual images taken at 100× magnification.

Human Leukocyte Antigens (HLA) HLA-A,B,C and HLA-DR are major determinants of allograft skin rejection. HLA-A,B,C are present on all nucleated cells in the body and were shown to be present in the non-keratinized epidermis and dermis in Fresh human skin by anti-HLA-A,B,C antibody and peroxidase staining (FIGS. 11 and 13). Staining was very intense and throughout the tissue. In contrast, no detectable positive staining for HLA-A,B,C was present at 100×, 200×, and 400× magnification in any of the decellularized skin samples (FIG. 11). HLA-DR, which is present on "antigen presenting cells" in the human body, was positively identified by anti-HLA-DR antibody and peroxidase staining mostly in the dermis of Fresh skin samples (FIG. 12). In contrast, no detectable positive staining for HLA-DR was present at 100×, 200×, and 400× magnification in any of the decellularized skin samples (FIG. 12). Composite images of complete sections of human skin before and after decellularization created by taking overlapping images at 100× magnification give a sense of the complete absence of positive staining for HLA-A,B,C (FIG. 13). This also represented the effect of decellularization on the removal of HLA-DR and therefore a separate composite for HLA-DR was not shown.

DNA Quantification

DNA analysis of Fresh human skin using the Quant-iT Picorgreen Assay Kit (Invitrogen, P7581) revealed a content of 650±131 ng/mg (dry wt) of tissue. In contrast, no detectable amount of DNA was present after decellularization by Aqueous or Ethanol protocols (Table 1). According to the manufacturer's directions, a lower detection level of <0.5 ng/mg (dry wt) was possible under our testing conditions.

Hydrothermal Isometric Temperature (HIT) Test

Samples of Fresh skin displayed a thermal denaturation temperature (Td) of 67.0±0.4° C. Decellularized skin processed by Aqueous (Td=67.1±0.8° C.) or Ethanol (Td=65.8±0.9° C.) protocols displayed similar thermal denaturation temperatures (Table 2). This indicated that the structure of collagen within the skin was unaltered by our decellularization methods.

Conclusions

Both Aqueous and Ethanol decellularization protocols were able to produce highly decellularized human skin. Analyses revealed that cell nuclei, major immunogenic cell proteins (HLA-DR and HLA-A,B,C), and DNA content were non-detectable using the methods described. Further, significant reductions in the cytoskeletal proteins vimentin and Beta-actin were achieved in decellularized skin. Finally, thermostability analysis of collagen revealed that the decellularization methods employed with human skin preserved the native structure of collagen within the tissue.

Example 2

Sterilization of Human Skin

Tissue banks process and store allografts by washing fresh tissues with antibiotic/antimycotic solutions followed by cryopreservation. These procedures have proven inadequate for sterilization. Cryopreservation has been shown by others to damage connective tissue structure [Kitagawa et al. (2001)]. Other sterilization techniques, such as ethylene oxide or gamma irradiation, have been shown to be deleterious to soft tissue grafts and are not generally used by others [Kearney, J. N. (2005); Azar, F. M. (2009)].

According to AATB Standards for Tissue Banking under K2.200 "Skin shall not be used for transplant if the following species are determined to be present: *Staphylococcus aureus, Streptococcus pyogenes* (group A strep.), *Enterococcus* sp., gram negative bacilli, *Clostridium*, and fungi (yeasts, molds)" [AATB (2006); (2008)]. In a study by Pianigiani et. al. (2009), they noted that the microorganisms responsible for skin allograft discard were all gram positives, the group of organisms most frequently isolated from pre-processing samples and included *Staphylococcus, Streptococcus, Enterococcus*, and *Bacillus* species. Four microorganisms were selected to determine if they can be removed and/or destroyed by our decellularization methods based on the American AATB Standards: *Staphylococcus aureus, Streptococcus pyogenes* (group A strep.), *Enterococcus* sp., and *Bacillus subtilis* which also was used as a surrogate for *Clostridium* due to its undesirable properties, such as odor and anaerobic culture conditions. *Bacillus* has been used as a surrogate for *Clostridium* in other studies [Stewart, Dunne, Skies, & Hoover, (2000)].

On the basis of on International Standards, ISO 11737-1 and 11737-2, a Standard Operating Procedure (SOP) of Bioburden Determination was developed in collaboration with professionals in the field of Microbiology. Preliminary experiments were first performed to validate the use of tools and techniques.

Materials and Methods

Removing Inhibition from Fresh Frozen Skin

Human skin collected by tissue banks is stored in a cocktail of antibiotics including Cefazolin and Gentomycin. To ensure complete removal of any inhibitory effects of the storage antibiotic cocktail, samples of fresh frozen human skin with a broad range of storage times were tested (4-31 days of storage). Inoculants for the four microorganisms used (*S. aureus, Streptococcus, Enterococcus*, and *Bacillus*) were prepared by first obtaining a correlation between optical density (OD) measured at 620 nm and the number of colony forming units (CFU)/mL. This was achieved by adjusting the OD value measured at 620 nm to 1 (acceptable range was 0.85 to 1.15) and spot plating the solution to check the concentration. A concentration/dilution factor was calculated from the correlation and used to make $10^8$ CFU/mL inoculants from a one OD suspension of bacteria.

Sterile PBS rinse and vortexing were chosen as the methods to remove residual antibiotics from skin allografts because these techniques had minimal effect on the number of microorganisms attached to the skin. The frequency of such washing treatments was dependent upon the degree of inhibition. Skin samples were subjected to different frequency of rinses with 10 mL of PBS or three-minute vortexing with 20 mL of PBS. To check the presence of any inhibitory antibiotics after washing with PBS, 100 µL of $10^8$ CFU/mL inoculants were added to a 50 mL centrifuge tube containing human skin and 10 mL sterile PBS. The tube was vortexed for one minute to allow release of antimicrobial substances from the skin. The working solution, which was already a $10^{-2}$ dilution of the original $10^8$ CFU/mL inoculants, was diluted by serial dilution. From the diluted solutions, six spots were made in Tryptic Soya Agar (TSA) plates by pipetting 100 µL of the solutions with $10^{-3}$ to $10^{-8}$ dilutions. The inoculant solution was also directly spot plated with dilutions from $10^{-3}$ to $10^{-8}$ for controls. Control plates of inoculants clearly showed the number of viable bacteria that should grow in the absence of inhibition.

Sterilization of Human Skin by Decellularization

Fresh frozen human skin from a total of four donors was procured, thawed at room temperature in its packaging, and prepared for treatment. From each donor, fifteen 4 cm×5 cm pieces (corresponding to 3 samples for each of the 4 microorganisms to be tested plus a negative control) and one 2 cm×5 cm (for bioburden background check) were prepared. Based upon the results of our inhibition study, fresh human skin to be inoculated with *S. aureus, Streptococcus* or used as a negative control were vortex for 3 minutes 6 times with 20 ml of sterile PBS; skin to be inoculated with *Enterococcus*, and *Bacillus* was vortex once with 20 mL of sterile PBS.

Inoculants ($10^8$ CFU/mL) for the four microorganisms used, *S. aureus, Streptococcus, Enterococcus*, and *Bacillus* were prepared as described previously under "Removing Inhibition from Fresh Frozen Skin" In a class II/III biological safety cabinet, a total of 400 µL of each inoculant solution was added to the dermal side of designated human skin samples (n=3 per microorganism) by pipetting 100 µL onto four quadrants and spreading evenly throughout the surface using a sterile transfer pipette. As a negative control, 400 µL of sterile PBS was added to 3 samples of human skin. The inoculated tissues were then left to stand under laminar flow without drying out (60-75 minutes) to ensure absorption of the bacterial inoculants. Samples of inoculated skin were then transferred to separate 500 mL containers corresponding to *S. aureus, Streptococcus, Enterococcus, Bacillus* or the PBS negative control with each container holding three 4 cm×5 cm samples. The samples of skin were then treated with the Aqueous Decellularization or Ethanol Decellularization, with or without Peractic Acid treatment as outlined below.

Specimens of inoculated fresh human skin were first treated with 300 mL of a hypotonic solution containing 10 mM Tris buffer (Trizma Base, T87602) and 5 mM ethylenediaminetetraacetic acid (EDTA, E9884) as a metalloprotease inhibitor. This solution was adjusted to pH=8 using HCl/NaOH prior to use. To this container was added 5 mL/L of a penicillin/streptomycin 100× solution (A5955, stock concentration of 10,000 U/mL/10,000 mg/mL) and 0.35 mL/L of a stock solution (5% w/v in 100% ethanol) of the serine protease inhibitor phenylmethanesulfonyl fluoride (PMSF, P7626) The container was then allowed to mix gently on a shaker table at 40-65 RPM, T=20-25° C., for 24 hours with fresh solution changed at 12 hours. During the first 12 hours of treatment, the epidermis of the skin samples is released from the underlying dermis and is removed from the container when the solution is refreshed.

The hypotonic solution was decanted and replaced with 300 mL of a high saline solution containing 5 M potassium chloride (KCl, P9541) 50 mM Tris buffer (T87602) containing 1% (v/v) Triton X-100 (octyl phenoxy polyethoxyethanol, T9284) and a metalloprotease inhibitor (5 mM of EDTA, E9884) This solution was adjusted to pH=8 using HCl/NaOH prior to use. To this container was added 5 mL/L of a penicillin/streptomycin 100× solution (A5955, stock concentration of 10,000 U/mL/10,000 mg/mL) and 0.35 mL/L of a stock solution (5% w/v in 100% ethanol) of the serine protease inhibitor phenylmethanesulfonyl fluoride (PMSF, P7626). The container was allowed to mix gently on a shaker table (at 40-65 RPM), T=20-25° C., for 36 hours with fresh solution changed every 12 hours.

To ensure sterility, all work from this point onward was carried out in a Class II/III biological safety cabinet using aseptic technique. The previous high saline solution was decanted and replaced with 300 mL of sterile deionized water. Specimens were rinsed for 30 minutes. Following the rinse, the sterile deionized water was decanted and replaced with 300 mL of sterile Hanks'/HEPES physiological buffer (0.14 M Sodium Chloride (S9625), 5.4 mM Potassium Chloride (P9541), 0.26 mM Sodium Phosphate dibasic (S0876), 0.44 mM Potassium Phosphate monobasic (P5379), 4.2 mM Sodium Bicarbonate (S8875), 10 mM HEPES Sodium salt (H7006), 8.3 mM Calcium Chloride dihydrate (C3881), 0.2 mM Magnesium Sulfate heptahydrate (M1880), and 0.25 mM Magnesium Chloride hexahydrate (M0250). This solution was adjusted to pH 7.35 using HCl/NaOH prior to use. Specimens were rinsed in the Hanks'/HEPES physiological buffer for 30 minutes.

The Hanks'/HEPES physiological buffer used for the rinse was decanted and replaced with 200 mL of Hanks'/HEPES physiological buffer containing 1330 µL of deoxyribonuclease stock solution (DNAse type II from bovine pancreas (D4527), 13.3 U/µL, in a 0.175 g NaCl (S9625)/10 mL glycerol (G7757)/10 mL sterile water solution adjusted to pH 7.3) and 1330 µL of ribonuclease stock solution (RNAse type III-A from bovine pancreas (R5125), 85 µg/mL, in a 0.03 g Trizma Base (T87602)/0.22 g NaCl (S9625)/25 mL sterile water solution adjusted to pH 7.5). The tissue was then placed in a shaking water bath, gently mixed (45-60 RPM) at 37° C. for 5 hours. After 5 hours the solution was decanted and replaced with fresh sterile Hanks'/HEPES physiological buffer, briefly rinsing the tissue.

The previous physiological buffer rinse was decanted and replaced by 300 mL of a either (i) a 50 mM Tris buffer (Trizma Base, T87602) solution in water adjusted to pH 9 and containing 1% (v/v) Tri-n-butyl phosphate (TnBP, 158615), 5 mL/L of a penicillin/streptomycin antibiotic/antimycotic 100× solution (stock concentration of 10,000 U/mL/10,000 mg/mL) with samples denoted as "Aqueous Decellularization" or (ii) a 50 mM Tris buffer (Trizma Base, T87602) solution in 70% Ethanol adjusted to pH 9 and containing 1% (v/v) Tri-n-butyl phosphate (TnBP, 158615) with samples denoted as "Ethanol Decellularization". The samples of tissue were then gently mixed on a shaker table (45-60 RPM) at T=20-25° C. for 48 hours with fresh solution changes every 12 hours.

After treatment, the solutions were decanted and refreshed with 300 mL of 50 mM Tris buffer (Trizma Base, T87602) solution, adjusted to pH 9 and containing 5 mL/L of a penicillin/streptomycin antibiotic/antimycotic 100× solution (stock concentration of 10,000 U/mL/10,000 mg/mL). The container was then allowed to mix gently on a shaker table (at 40-65 RPM), T=20-25° C., for 24 hours with fresh solution changed at 12 hours.

Next, the previous pH 9 Tris buffer solution was decanted and replaced with 300 mL of either a (i) 1% (v/v) Peracetic Acid (PAA) solution in ethanol (PAA solution consisted of 2% peracetic acid (269336), 100% ethanol, and sterile water (ratio v/v/v 2/1/1), providing a final sterilization solution of 1% PAA) or (ii) directly into a fresh sterile phosphate-buffered saline (PBS) solution containing 0.14 M sodium chloride (NaCl, S9625), 2.7 mM potassium chloride (KCl, P9541), 6.5 mM sodium phosphate dibasic (S0876), 1.5 mM potassium phosphate monobasic (P5379), adjusted to pH 7.4, and containing 5 mL/L of a penicillin/streptomycin antibiotic/antimycotic 100× solution (stock concentration of 10,000 U/mL/10,000 mg/mL). The container was allowed to mix gently on a shaker table (at 40-65 RPM), T=20-25° C., for 12 hours. After, the tissue specimens were rinsed twice (30 minutes each) with 300 mL of fresh sterile phosphate buffered saline solution containing no antibiotics/antimycotics. For the Peracetic Acid treatment, samples were treated for 4 hours, mixing gently on a shaker table (at 40-65 RPM), at T=20-40° C. After PAA treatment, the samples were placed in fresh sterile phosphate-buffered saline (PBS) solution adjusted to pH 7.4, and containing 5 mL/L of a penicillin/streptomycin antibiotic/antimycotic 100× solution (stock concentration of 10,000 U/mL/10,000 mg/mL). The container was allowed to mix gently on a shaker table (at 40-65 RPM), T=20-25° C., for 12 hours. After, the tissue specimens were rinsed twice (30 minutes each) with 300 mL of fresh sterile phosphate buffered saline solution containing no antibiotics/antimycotics.

Samples of Aqueous Decellularized and Ethanol Decellularized skin, with or without Peracetic Acid treatment were then immediately analyzed for the presence of *S. aureus, Streptococcus, Enterococcus*, and *Bacillus* as outlined below. Samples inoculated with sterile PBS only served as a negative control.

Detection and Enumeration of Bioburden

Samples (2×2.5 cm pieces) of human skin from each 500 mL container corresponding to each decellularization method (Aqueous Decellularized and Ethanol Decellularized skin, with or without Peracetic Acid treatment) and microorganism inoculant (*S. aureus, Streptococcus, Enterococcus, Bacillus* or the PBS negative control) were prepared. Two samples of skin per treatment, per microorganism inoculant, were directly plated on Tryptic Soya Agar (TSA) plates. One sample of skin per treatment, per microorganism inoculant was placed into a 50 mL polypropylene tube for bacterial quantification. To the tube was added 10 mL of sterile PBS and the tube sonicated for 5 minutes and Vortex for 1 minute to release the bacteria. Dilutions of the supernatant were created ($10^{-3}$ to $10^{-8}$) and spot plated onto TSA plates. The remaining "washed" skin was aseptically transferred onto TSA plates without excess liquid for direct plating. According to AATB guidelines [AATB (2006); (2008)], all plates were incubated at 37° C. for 7 days and the presence or absence of bacterial colonies noted.

Further, to corroborate our findings, a 2×2.5 cm sample of human skin from each 500 mL container corresponding to each microorganism inoculant (*S. aureus, Streptococcus, Enterococcus, Bacillus* or the PBS negative control) for decellularization Ethanol Decellularized skin with Peracetic Acid treatment were sent to the Department of Pathology and Laboratory Medicine, Capital District Health Authority, Halifax, Nova Scotia, Canada for analysis according to the American Association of Tissue Banks (AATB) Standards ($12^{th}$ edition) for human skin. Testing included the detection of bacteria, yeast, or fungi. Samples were incubated at 35° C. for 7 days for bacteria and at 30° C. for 30 days for yeast or fungi in their respective media, with readings taken on a daily basis. If positive growth was detected at any time, subculturing was performed to identify the species of microbial contaminant.

As a positive control to show that decellularized skin was capable of supporting bacterial growth, samples of decellularized skin were also inoculated with each of the four species of bacteria used in this assay. The samples were then placed into a 50 mL polypropylene tube for bacterial quantification. To the tube was added 10 mL of sterile PBS and the tube sonicated for 5 minutes and Vortex for 1 minute to release the bacteria. Dilutions of the supernatant were created ($10^{-3}$ to $10^{-8}$) and spot plated onto TSA plates. The remaining "washed" skin was aseptically transferred onto TSA plates without excess liquid for direct plating. The plates were incubated at 37° C. for 1 day and the presence or absence of bacterial colonies noted.

Results

Controls

In all cases, negative controls (TSA plates alone, human skin inoculated with PBS) did not reveal the presence of bacterial colonies. Further, background level measurements for *Staphylococcus aureus, Streptococcus pyogenes* (group A strep.), *Enterococcus* sp., and *Bacillus subtilis* revealed an absence of bacteria. For positive controls, decellularized human skin inoculated with each of the four species of bacteria was shown to be positive after only 1 day of incubation in both the wash solutions and by direct plating of the decellularized skin (Table 4).

Decellularization Methods

Decellularization of human skin by Aqueous and Ethanol protocols after inoculation with $10^8$ CFU/mL of *Staphylococcus aureus, Streptococcus pyogenes* (group A strep.), *Enterococcus* sp., and *Bacillus subtilis* was shown to eliminate all species but *Bacillus subtilis* (data not shown). When a 1% (v/v) peracetic acid treatment step was added to the decellularization protocol, complete removal of all microbial species was obtained with a greater than 6 log 10 reduction in bacterial load achieved as shown by the complete absence of bacteria in the wash solutions, by direct plating of the washed skin (labeled "Skin"), and by direct plating of unwashed skin (labeled "Direct Plating") (Table 3).

Table 5 shows the results of third-party testing (Department of Pathology and Laboratory Medicine, Capital District Health Authority, Halifax, Nova Scotia, Canada) for the presence of microorganisms according to the guidelines of the American Association of Tissue Banks (AATB). Decellularization of human skin by Ethanol Decellularization protocol with Peracetic acid treatment after inoculation with $10^8$ CFU/mL of *Staphylococcus aureus, Streptococcus pyogenes* (group A strep.), *Enterococcus* sp., and *Bacillus subtilis* was shown to completely remove all microbial species. In all samples, no bacteria or fungi were detected.

Conclusions

Decellularization by Aqueous or Ethanol Decellularization protocols on their own did not achieve complete removal of all four species of bacteria (*Staphylococcus aureus, Streptococcus pyogenes* (group A strep.), *Enterococcus* sp., and *Bacillus subtilis*) used in inoculants on fresh skin. Complete removal of all four bacterial species was obtained after the inclusion of a 1% (v/v) peracetic acid rinse to the decellularization protocols producing a human decellularized skin graft acceptable for transplant according to the American Association of Tissue Banks (AATB) standards [AATB (2006); (2008)].

Example 3

Decellularization and Sterilization of Human Fascia

Human fascia is procured and prepared for treatment. The extent of tissue preparation is dependent upon the quality of the fascia obtained, but usually involves removing extraneous tissue elements and cutting the fascia to size(s) required by end users. For this example, three specimens of human fascia are treated in one container. The size of the specimens used is 4 cm×5 cm and tissues are treated with a minimum volume ratio of solution to tissue of 50:1. Specimens are transferred to a lidded polypropylene jar containing a preferred volume of 300 mL of a hypotonic (<300 mmol/L preferred value of 10 mM) Tris buffer and a metalloprotease inhibitor at a concentration of 1 µM-25 mM (preferred value of 5 mM and inhibitor being used is ethylenediaminetetraacetic acid (EDTA)). This solution is adjusted to pH 7-9 (preferred at pH=8) using HCl/NaOH prior to use. To this container is added antibiotics/antimycotics at 50-100 U/mL or 50-100 µg/mL dependent upon agent (preferred using 5 mL/L of a penicillin/streptomycin 100× solution with a stock concentration of 10,000 U/mL/10,000 mg/mL) and protease inhibitor (preferred value of 0.35 mL/L of the serine protease inhibitor (5% phenylmethanesulfonyl fluoride in 100% ethanol)). The container is allowed to mix gently on a shaker table at 40-65 RPM, T=20-25° C., for 24 hours with fresh solution changed at 12 hours. This stage is designed to cause the cells in the tissue to absorb water (hypotonic conditions) and eventually burst.

Next, the previous hypotonic solution is decanted and replaced with a minimum volume ratio of solution to tissue of 50:1 (preferred 300 mL) of a high saline solution (preferred value of 1.5 M of potassium chloride with 50 mM Tris buffer) containing 1% (v/v) Triton X-100 (octyl phenoxy polyethoxyethanol), metalloprotease inhibitor at a concentration of 1 µM-25 mM (preferred value of 5 mM of EDTA) and protease inhibitor (preferred value of 0.35 mL/L of the serine protease inhibitor (5% phenylmethanesulfonyl fluoride in 100% ethanol)). To the container is added antibiotics/antimycotics at 50-100 U/mL or 50-100 µg/mL dependent upon agent (preferred using 5 mL/L of a penicillin/streptomycin 100× solution with a stock concentration of 10,000 U/mL/10,000 mg/mL). The container is allowed to mix gently on a shaker table (at 40-65 RPM), T=20-25° C., for 36 hours with fresh solution changed every 12 hours. This stage of the treatment is designed to remove cell membranes and cytoskeletal components.

To ensure sterility, all work from this point onward is carried out in a Class II/III biological safety cabinet using aseptic technique. The previous high saline solution is decanted and replaced with a minimum volume ratio of solution to tissue of 50:1 (preferred value of 300 mL) of sterile deionized water. Specimens are rinsed for 30 minutes. Following the rinse with sterile deionized water, it is replaced with a minimum volume ratio of solution to tissue of 50:1 (preferred value of 300 mL) of Hanks'/HEPES physiological buffer (0.14 M Sodium Chloride, 5.4 mM Potassium Chloride, 0.26 mM Sodium Phosphate dibasic, 0.44 mM Potassium Phosphate monobasic, 4.2 mM Sodium Bicarbonate, 10 mM HEPES Sodium salt, 8.3 mM Calcium Chloride dihydrate, 0.2 mM Magnesium Sulfate heptahydrate, and 0.25 mM Magnesium Chloride hexahydrate. This solution is adjusted to pH 7.35 using 2 M HCl/NaOH prior to use). Specimens are rinsed in physiological buffer for 30 minutes.

Following this rinse, the physiological buffer is decanted and replaced with 200 mL of Hanks'/HEPES physiological buffer. To this is added endonucleases, preferred DNAse and RNAse, at preferred quantities of 1330 µL of deoxyribonuclease stock (type II from bovine pancreas, 13.3 U/µL NaCl/glycerol pH 7.3 solution and 1330 µL of ribonuclease stock (type III-A from bovine pancreas, 85 µg/mL). The tissue is then placed in a shaking water bath, gently mixed (45-60 RPM) at 37° C. for 5 hours. After 5 hours the solution is decanted and replaced with fresh Hanks'/HEPES physiological buffer, briefly rinsing the tissue. This stage of the process is designed to degrade DNA and RNA to facilitate their subsequent removal.

The previous physiological buffer rinse is decanted and replaced by 300 mL of a 50 mM Tris buffer solution adjusted to pH 9 and containing 1% (v/v) Tri-n-butyl phosphate (TnBP). To the container is then added 1.5 mL of a penicillin/streptomycin antibiotic/antimycotic 100× solution (stock concentration of 10,000 U/mL/10,000 mg/mL). This step of the decellularization treatment can also be performed using a solution made up as 1% (v/v) TnBP in 70% ethanol without antibiotics/antimycotics. The tissue then gently mixed on a shaker table (45-60 RPM) at T=20-25° C. for 48 hours with fresh solution changes every 12 hours. This stage is designed to further remove any remaining cellular components (cytoskeletal proteins, DNA, RNA) as TnBP is a "surfactant like" chaotropic solvent. Further, TnBP has been shown to deactivate viruses.

After treatment, the solution is decanted and refreshed with 300 mL of 50 mM Tris buffer solution adjusted to pH 9 (containing no TnBP). The same amount of antibiotic/antimycotic solution (penicillin/streptomycin) previous used is added and the container is allowed to mix gently on a shaker table (at 40-65 RPM), T=20-25° C., for 24 hours with fresh solution changed at 12 hours.

Next, the previous pH 9 Tris buffer solution is decanted and replaced with 300 mL of a 1% (v/v) Peracetic Acid (PAA) solution in ethanol (PAA solution consisted of 2% peracetic acid, 100% ethanol, and sterile water (ratio v/v/v 2/1/1), providing a final sterilization solution of 1% PAA) for 4 hours, mixing gently on a shaker table (at 40-65 RPM), at T=20-40° C. After PAA treatment, fresh sterile phosphate-buffered saline solution (PBS, containing 0.14 M sodium chloride, 2.7 mM potassium chloride, 6.5 mM sodium phosphate dibasic, 1.5 mM potassium phosphate monobasic and is adjusted to pH 7.4). The same amount of antibiotic/antimycotic (penicillin/streptomycin) solution used previously is added and the container is allowed to mix gently on a shaker table (at 40-65 RPM), T=20-25° C., for 12 hours. After, the specimen is rinsed twice for 30 minutes each with 300 mL fresh sterile phosphate buffered saline solution at room temperature containing no antibiotics/antimycotics.

In a final step, the each piece of tissue is bottled under sterile conditions with a minimum volume ratio of solution to tissue of 20:1 to 50:1 in either (i) fresh sterile phosphate buffered saline solution infused with penicillin/streptomycin (6 mL/L of 100× solution with a stock concentration of 10,000 U/mL/10,000 mg/mL) solution or (ii) 70% ethanol and stored at 4° C.

These processes produce decellularized and sterilized human fascia. Analyses similar to those employed in the Examples above and/or known in the art reveal that cell nuclei, major immunogenic cell proteins (e.g., HLA-DR and HLA-A,B,C), and DNA content are substantially reduced compared to controls. Further, significant reductions in the cytoskeletal proteins such as, e.g., vimentin and Beta-actin, are achieved compared to controls. Thermostability analysis of collagen reveals that the decellularization methods largely preserve the native structure of collagen within the fascia. Decellularization by, e.g., Aqueous or Ethanol Decellularization protocols, also reduces the amount of bacteria (*Staphylococcus aureus, Streptococcus pyogenes* (group A strep.), *Enterococcus* sp., and *Bacillus subtilis*). Removal of all four bacterial species is obtained via inclusion of a 1% (v/v) peracetic acid rinse. The resulting fascia graft is acceptable for transplant according to the guidelines provided by the American Association of Tissue Banks (AATB) standards [AATB (2006); (2008)].

Example 4

Decellularization and Sterilization of Soft Tissue

Tissue (e.g., a human soft tissue) is harvested and prepared for treatment. The extent of tissue preparation is dependent upon the tissue to treated, but usually involves removing extraneous tissue elements and cutting the tissue to size in order to facilitate decellularization. Specimens are then immersed in a hypotonic salt (<300 mol/L) solution, pH=7-9, with anti-proteolytic agents whose concentration are dependent upon inhibitor used (phenylmethanesulfonylfluoride (PMSF), aprotinin, leupeptin, Ethylenediamineteteraacetic acid (EDTA)), anti-microbial agents (penicillin, vancomycin, streptomycin, gentamycin, kanamycin, neomycin, sodium azide ($NaN_3$)) with or without anti-fungal agents (Amphotericin B, Nystain) prepared with at minimum type II cell culture grade deionized water. The tissue is treated with a minimum volume ratio of solution to tissue of 20:1 to 50:1, on a rotating shaker table at 40-65 RPM, for 24-48 hours, T=4-40° C., with solution changes at minimum occurring at 12 hour intervals.

The tissue is then transferred to a high saline (>1 M, NaCl, KCl) buffered solution (pH=8-10) containing 0.2-3% (v/v) of a anionic, non-ionic, zwitterionic or cationic detergent (Triton X-100, Triton X-200, Tween 20, Tween 80, sodium deoxycholate, CHAPS, sodium dodecyl sulfate (SDS), N-lauroyl-sarcosinate, Igepal CA630, Sulfobetain-10 and -16) and protease inhibitors (candidates as listed above) prepared with at minimum type II cell culture grade deionized water. The tissue is treated with a minimum volume ratio of solution to tissue of 20:1 to 50:1, on a rotating shaker table at 40-65 RPM, for 24-48 hours, T=4-40° C., with solution changes at minimum occurring at 12 hour intervals.

The tissue is then subjected to rinses with sterile physiological buffer (Hanks' Balanced Salt Solution (HBSS), HEPES, Phosphate Buffered Saline (PBS), Tris-Buffered Saline (TBS)) pH=6-8, T=4-40° C., 5 minutes to 1 hour, and then treated with a solution of endonucleases (DNAse, RNAse, Benzonase) prepared in a physiological buffer (Hanks' Balanced Salt Solution (HBSS), HEPES, Phosphate Buffered Saline (PBS), Tris-Buffered Saline (TBS)), pH=6-8, for 1-5 hours, T=20-40° C. Afterward, the tissue is rinsed in sterile physiological buffer alone as specified above for 5 minutes-1 hour, T=4-40° C.

In the next stage, the tissue is treated with a sterile solution of 0.2-3% (v/v) anionic, non-ionic, zwitterionic or cationic detergent (Triton X-100, Triton X-200, Tween 20, Tween 80, sodium deoxycholate, CHAPS, sodium dodecyl sulfate (SDS), N-lauroyl-sarcosinate, Igepal CA630, Sulfobetain-10 and -16) or chaotropic agent (Tri-n-butyl phosphate (TnBP)) prepared in either (i) physiological buffer solution (Hanks' Balanced Salt Solution (HBSS), HEPES, Phosphate Buffered Saline (PBS), Tris-Buffered Saline (TBS)) adjusted to pH=7-9 with anti-microbial agents (penicillin, vancomycin, streptomycin, gentamycin, kanamycin, neomycin, sodium azide ($NaN_3$)) with or without anti-fungal agents (Amphotericin B, Nystain) or with (ii) 50-70% ethanol, for 24-48 hours at T=4-40° C. Afterward, the tissue is rinsed with a sterile 50 mM Tris buffer solution adjusted to pH 9 (containing no detergent or chaotropic agent) for 12-24 hours at T=4-40° C.

Next the tissue is treated with a 0.05-3% (v/v) Peracetic Acid (PAA) solution in ethanol or Phosphate Buffered Saline (PBS) neutralized to pH=7 to 7.5, for a duration of 30 minutes to 4 hours at T=20-40° C. After, the tissue is rinsed with sterile physiological buffer (Hanks' Balanced Salt Solution (HBSS), HEPES, Phosphate Buffered Saline (PBS), Tris-Buffered Saline (TBS)) with anti-microbial agents (penicillin, vancomycin, streptomycin, gentamycin, kanamycin, neomycin, sodium azide ($NaN_3$)) with or without anti-fungal agents (Amphotericin B, Nystain) for 12-24 hours at T=4-40° C.

Finally, tissues are bottled under sterile conditions in either (i) sterile physiological buffer (Hanks' Balanced Salt Solution (HBSS), HEPES, Phosphate Buffered Saline (PBS), Tris-Buffered Saline (TBS)) with anti-microbial agents (penicillin, vancomycin, streptomycin, gentamycin, kanamycin, neomycin, sodium azide ($NaN_3$)) with or without anti-fungal agents (Amphotericin B, Nystain) or (ii) 50-70% ethanol and stored at T=4-25° C.

These processes produce decellularized and sterilized tissue. Analyses similar to those employed in the Examples above and/or known in the art reveal that cell nuclei, major immunogenic cell proteins (e.g., HLA-DR and HLA-A,B, C), and DNA content are substantially reduced compared to controls. Further, significant reductions in the cytoskeletal proteins such as, e.g., vimentin and Beta-actin, are achieved compared to controls. Thermostability analysis of collagen reveals that the decellularization methods largely preserve the native structure of collagen within the tissue. Decellularization by, e.g., Aqueous or Ethanol Decellularization protocols, also reduces the amount of bacteria (*Staphylococcus aureus, Streptococcus pyogenes* (group A strep.), *Enterococcus* sp., and *Bacillus subtilis*). Removal of all four bacterial species is obtained via inclusion of a 1% (v/v) peracetic acid rinse. The resulting graft is acceptable for transplant according to the guidelines provided by the American Association of Tissue Banks (AATB) standards [AATB (2006); (2008)].

All publications and patent applications cited in this specification are herein incorporated by reference in their entirety for all purposes as if each individual publication or patent application were specifically and individually indicated to be incorporated by reference for all purposes.

Although the foregoing present disclosure has been described in some detail by way of illustration and example for purposes of clarity of understanding, it will be readily apparent to one of ordinary skill in the art in light of the teachings of this present disclosure that certain changes and modifications can be made thereto without departing from the spirit or scope of the appended claims.

Tables

TABLE 1

Results of the DNA Assay indicating removal of cellular DNA from human skin samples to below detection levels (0.5 ng/mg dry wt of tissue) after decellularization treatment.

| Sample | DNA Content in ng/mg (dry wt) of tissue |
|---|---|
| Fresh Human Skin | 650 ± 131 |
| Aqueous Decellularization Method | None Detected** |
| Ethanol Decellularization Method | None Detected** |

**None detected is <0.25 ng/ml or <0.5 ng/mg (ppm) dry wt, the lowest standard detected by the PicoGreen ® DNA Assay (Invitrogen ™ Molecular Probes ®) using a 10 mg dry wt of sample.

TABLE 2

Hydrothermal Isometric Tension (HIT) Test Results

| Donor | HIT Inflection (° C.) or Denaturation Temperature | | |
|---|---|---|---|
| | Fresh | Aqueous | 70% Ethanol |
| TD09-163 | 67.5 | 68 | 66 |
| TD09-195 | 66.5 | 66.5 | 66 |
| TD09-196 | 67 | 67.5 | 64.5 |
| TD09-242 | 67 | 66.5 | 66.5 |
| Average ± SD | 67.0 ± 0.4 | 67.1 ± 0.8 | 65.8 ± 0.9 |

The HIT test is a measure of the stability of collagen within soft tissues. If our process had altered the structure of collagen (the main component in human dermis), then we would see a significant drop in the Denaturartion Temperature of the decellularized human skin. The data shown above from 4 different donors indicates that there is no change in collagen stability and therefore collagen structure, after decellularization treatment.

TABLE 3a-d

Results of bioburden microbiology assay after 7 days of incubation. Samples of fresh human skin from 4 donors-(a) TD10-238, (b) TD10-272, (c)TD09-195, (d) TD10-240-were each inoculated with 400 µL of solution containing $10^8$ CFU/mL of *S. Aureaus*, *Streptococcus*, *Enterococcus*, or *Bacillus*. The samples of fresh skin were then decellularized using the process outlined in FIG. 1. After decellularization, samples were washed with 10 mL of sterile phosphate buffered saline (PBS) and serial dilutions ($10^{-3}$ to $10^{-8}$) of the PBS wash were spot plated onto Tryptic Soy Agar (TSA plates). The PBS washed skin (labelled "Skin") and a sample of decellularized skin not washed with PBS (labelled "Direct Plating") were also direct plated onto TSA plates. All TSA plates were incubated for 7 days. No colonies of bacteria were detected in PBS solutions used to rinse the decellularized skin or by direct plating of decellularized skin. Negative controls consisted of TSA plates alone.

| Micro-organism | Concentration of Wash solution | | | | | | Skin | Direct Plating |
|---|---|---|---|---|---|---|---|---|
| | $10^{-3}$ | $10^{-4}$ | $10^{-5}$ | $10^{-6}$ | $10^{-7}$ | $10^{-8}$ | | |

Table 3(a) Donor TD10-238

| | | | | | | | | |
|---|---|---|---|---|---|---|---|---|
| S. Aureus | 0 | 0 | 0 | 0 | 0 | 0 | 0 | 0 |
| Streptococcus | 0 | 0 | 0 | 0 | 0 | 0 | 0 | 0 |
| Enterococcus | 0 | 0 | 0 | 0 | 0 | 0 | 0 | 0 |
| Bacillus | 0 | 0 | 0 | 0 | 0 | 0 | 0 | 0 |
| Negative Control | 0 | 0 | 0 | 0 | 0 | 0 | 0 | 0 |

Table 3(b) Donor TD10-272

| | | | | | | | | |
|---|---|---|---|---|---|---|---|---|
| S. Aureus | 0 | 0 | 0 | 0 | 0 | 0 | 0 | 0 |
| Streptococcus | 0 | 0 | 0 | 0 | 0 | 0 | 0 | 0 |
| Enterococcus | 0 | 0 | 0 | 0 | 0 | 0 | 0 | 0 |
| Bacillus | 0 | 0 | 0 | 0 | 0 | 0 | 0 | 0 |
| Negative Control | 0 | 0 | 0 | 0 | 0 | 0 | 0 | 0 |

Table 3(c) Donor TD09-195

| | | | | | | | | |
|---|---|---|---|---|---|---|---|---|
| S. Aureus | 0 | 0 | 0 | 0 | 0 | 0 | 0 | 0 |
| Streptococcus | 0 | 0 | 0 | 0 | 0 | 0 | 0 | 0 |
| Enterococcus | 0 | 0 | 0 | 0 | 0 | 0 | 0 | 0 |
| Bacillus | 0 | 0 | 0 | 0 | 0 | 0 | 0 | 0 |
| Negative Control | 0 | 0 | 0 | 0 | 0 | 0 | 0 | 0 |

Table 3(d) Donor TD10-240

| | | | | | | | | |
|---|---|---|---|---|---|---|---|---|
| S. Aureus | 0 | 0 | 0 | 0 | 0 | 0 | 0 | 0 |
| Streptococcus | 0 | 0 | 0 | 0 | 0 | 0 | 0 | 0 |
| Enterococcus | 0 | 0 | 0 | 0 | 0 | 0 | 0 | 0 |
| Bacillus | 0 | 0 | 0 | 0 | 0 | 0 | 0 | 0 |
| Negative Control | 0 | 0 | 0 | 0 | 0 | 0 | 0 | 0 |

TABLE 4a-d

Results of microbiology assay for inoculation positive controls. Samples of decellularized human skin from 4 donors-(a) TD10-238, (b) TD10-272, (c)TD09-195, (d) TD10-240-were each inoculated with 400 µL of solution containing $10^8$ CFU/mL of *S. Aureaus*, *Streptococcus*, *Enterococcus*, or *Bacillus*. The samples were washed with 10 mL of sterile phosphate buffered saline (PBS) and serial dilutions ($10^{-3}$ to $10^{-8}$) of the PBS wash were spot plated onto Tryptic Soy Agar (TSA plates). The PBS washed skin (labelled "Skin") was also direct plated onto TSA plates. All TSA plates were incubated for 24 hours and the number of colonies determined. All samples showed positive bacterial growth indicating that inoculated bacteria will grow on decellularized tissue.

| Micro-organism | Concentration of Wash solution | | | | | | Skin |
|---|---|---|---|---|---|---|---|
| | $10^{-3}$ | $10^{-4}$ | $10^{-5}$ | $10^{-6}$ | $10^{-7}$ | $10^{-8}$ | |

Table 4(a) Donor TD10-238

| | | | | | | | |
|---|---|---|---|---|---|---|---|
| S. Aureus | TNTC | TNTC | TNTC | 52 | 9 | 0 | TNTC |
| Streptococcus | TNTC | TNTC | TNTC | 127 | 12 | 1 | TNTC |
| Enterococcus | TNTC | TNTC | TNTC | 72 | 7 | 1 | TNTC |
| Bacillus | TNTC | TNTC | TNTC | 24 | 2 | 1 | TNTC |

Table 4(b) Donor TD10-272

| | | | | | | | |
|---|---|---|---|---|---|---|---|
| S. Aureus | TNTC | TNTC | TNTC | 80 | 11 | 0 | TNTC |
| Streptococcus | TNTC | TNTC | TNTC | 103 | 12 | 1 | TNTC |
| Enterococcus | TNTC | TNTC | TNTC | 61 | 7 | 1 | TNTC |
| Bacillus | TNTC | TNTC | TNTC | 33 | 2 | 0 | TNTC |

Table 4(c) Donor TD09-195

| | | | | | | | |
|---|---|---|---|---|---|---|---|
| S. Aureus | TNTC | TNTC | TNTC | 59 | 8 | 1 | TNTC |
| Streptococcus | TNTC | TNTC | TNTC | 90 | 6 | 0 | TNTC |

TABLE 4a-d-continued

Results of microbiology assay for inoculation positive controls. Samples of decellularized human skin from 4 donors-(a) TD10-238, (b) TD10-272, (c)TD09-195, (d) TD10-240-were each inoculated with 400 μL of solution containing $10^8$ CFU/mL of S. Aureaus, Streptococcus, Enterococcus, or Bacillus. The samples were washed with 10 mL of sterile phosphate buffered saline (PBS) and serial dilutions ($10^{-3}$ to $10^{-8}$) of the PBS wash were spot plated onto Tryptic Soy Agar (TSA plates). The PBS washed skin (labelled "Skin") was also direct plated onto TSA plates. All TSA plates were incubated for 24 hours and the number of colonies determined. All samples showed positive bacterial growth indicating that inoculated bacteria will grow on decellularized tissue.

| Micro-organism | Concentration of Wash solution | | | | | | |
|---|---|---|---|---|---|---|---|
| | $10^{-3}$ | $10^{-4}$ | $10^{-5}$ | $10^{-6}$ | $10^{-7}$ | $10^{-8}$ | Skin |
| coccus | | | | | | | |
| Enterococcus | TNTC | TNTC | TNTC | 71 | 8 | 1 | TNTC |
| Bacillus | TNTC | TNTC | TNTC | 23 | 1 | 0 | TNTC |
| Table 4(d) Donor TD10-240 | | | | | | | |
| S. Aureus | TNTC | TNTC | TNTC | 57 | 6 | 0 | TNTC |
| Streptococcus | TNTC | TNTC | TNTC | 88 | 4 | 0 | TNTC |
| Enterococcus | TNTC | TNTC | TNTC | 88 | 4 | 0 | TNTC |
| Bacillus | TNTC | TNTC | TNTC | 30 | 3 | 1 | TNTC |

Note:
TNTC = Too Numerous To Count.

TABLE 5

| | Microorganism | | | | |
|---|---|---|---|---|---|
| Donor | S. Aureus | Streptococcus | Enterococcus | Bacillus | Fungus |
| TD10-238 | No Growth | No Growth | No Growth | No Growth | No Fungi |
| TD10-195 | No Growth | No Growth | No Growth | No Growth | No Fungi |
| TD10-272 | No Growth | No Growth | No Growth | No Growth | No Fungi |

Table 5. Results of third-party testing for bioburden removal. Samples of fresh skin (2 cm × 2.5 cm) from 3 different donors were each inoculated with 400 μL of solution containing $10^8$ CFU/mL of S. Aureaus, Streptococcus, Enterococcus, or Bacillus. The samples of fresh skin were then decellularized using the process outlined in FIG. 1. After decellularization, samples were sent to the Department of Pathology and Laboratory Medicine, Capital DistrictHealth Authority, Halifax, Nova Scotia, Canada for analysis according to the American Association of Tissue Banks (AATB) Standards ($12^{th}$ edition). In all samples, no bacteria or fungi were detected.

REFERENCES

Lee J M, Pereira C A, Abdulla D, Naimark W A, Crawford I. (1995) A multi-sample denaturation temperature tester for collagenous biomaterials. *Med Eng Phys* 17: 115-121

(AATB) American Association of Tissue Banks (2008), Standards for Tissue Banking 12th edition. McLean (VA)

(AATB) American Association of Tissue Banks (2006), Guidance Document: Current Good Tissue Practice No. 3 Jun. 27, 2006

Pianigiani, E., Ierardi, F., Cuciti, C., Brignali, S., Oggioni, M., & Fimiani, M. (2009). Processing efficacy in relation to microbial contamination of skin allograft from 723 donors. *Burns*, 36(3), 347-351.

Stewart, C. P., Dunne, A., Skies, A., & Hoover, D. G. (2000). Sensitivity of spores of *Bacillus subtilis* and *Clostridium sporogenes* PA3679 to combinations of high hydrostatic pressure and other processing parameters. *Innovative Food Science Emergency Technology*, 1, 49-56.

ISO 11737-1 "Sterilization of medical devices-Microbiological methods—Part1: Determination of a population of microorganisms on products", $2^{nd}$ edition, Apr. 1, (2006)

ISO 11737-2 "Sterilization of medical devices-Microbiological methods—Part1: Tests of sterility performed in the definition, validation and maintenance of a sterilization process", $2^{nd}$ edition, November 15, (2009)

MacLean, S. B. A and Gratzer, P. F. (2011) "Effect of basic fibroblast growth factor (bFGF) on the cellular repopulation of decellularized ACL allografts" *Journal of Tissue Engineering and Regenerative Medicine*, 5:201-200

P. F. Gratzer, R. D. Harrison, T. Woods (2006) "Disruption of the Extracellular Matrix by SDS and Not Residual Toxicity Prevents Cellular Infiltration of Acellularized Tissues" *Tissue Engineering* 12(10): 2975-2983

T. Woods and P. F. Gratzer (2005) "Effectiveness of Three Extraction Techniques in the Development of an Acellular Bone-Anterior Cruciate Ligament (ACL)-Bone Graft" *Biomaterials* 26: 7339-49

R. D. Harrison P. F. Gratzer (2005) "Cellular Repopulation of a Naturally Derived Extracellular Matrix Scaffold for Anterior Cruciate Ligament Replacement" *Journal of Biomedical Materials Research*, 75A: 841-54

S. B. A. MacLean, P. F. Gratzer (2006) "Comparison of Seeding Methods Used in the Repopulation of Decellularized Porcine Anterior Cruciate Ligament Tissue", Proceedings of the 25th Canadian Biomaterials Society, May 26-28th, University of Calgary, Calgary, Alberta S. B. A. MacLean, P. F. Gratzer (2006) "Repopulation of decellularized porcine anterior cruciate ligaments with porcine ACL fibroblasts: A study into the effects of seeding methodology and the use of basic fibroblast growth factor (bFGF)", Regenerate: World Congress on Tissue Engineering and Regenerative Medicine, April 25th-27th, Pittsburgh, Pa., USA S. B. A. MacLean, P. F. Gratzer (2005) "The In vitro Application of Basic Fibroblast Growth Factor (bFGF) for Repopulation of the Decellularized Porcine Anterior Cruciate Ligament (ACL)", 55th Canadian Chemical Engineering Conference, October 16-19th, Toronto, Ontario C. R. Dyck, P. F. Gratzer (2005) "Validation of a Decellularized B-ACL-B rat Model for ACL Allograft Regeneration Studies", 55th Canadian Chemical Engineering Conference, October 16-19th, Toronto, Ontario C. R. Dyck, P. F. Gratzer (2006) "Use of Bone Marrow Stromal Cells to Repopulate Decellularized Anterior Cruciate Ligaments", Proceedings of the 25th Canadian Biomaterials Society, May 26-28th, University of Calgary, Calgary, Alberta

What is claimed:

1. A method for producing a human bioprosthetic tissue comprising:
   contacting a human tissue with a hypotonic solution to produce a lysed tissue, the human tissue having an epidermal cellular layer with an underlying dermis and an underlying basement membrane matrix;

contacting the lysed tissue with a first surfactant solution to produce a surfactant-treated tissue;

contacting the surfactant-treated tissue with a nuclease enzyme solution to produce an enzyme-treated tissue;

contacting the enzyme-treated tissue with a cleaning solution comprising a second surfactant, a chaotropic agent, or a mixture thereof, to produce a decellularized tissue; and contacting the decellularized tissue with a bioburden reducing agent solution to produce the human bioprosthetic tissue, wherein the bioburden reducing agent solution comprises 1% v/v Peracetic Acid;

wherein the human tissue's epidermal cellular layer has been removed, leaving the underlying basement membrane matrix intact in the human bioprosthetic tissue.

2. The method of claim 1, wherein the human tissue is human skin tissue, wherein the hypotonic solution comprises 10 mM Tris buffer, wherein the first surfactant solution comprises 1% v/v Triton X-100®, wherein the nuclease enzyme solution comprises RNase and DNase, wherein the cleaning solution comprises 1% v/v tri-n-butyl phosphate, wherein the bioburden reducing agent solution comprises 1% v/v Peracetic Acid, wherein each step of the method is performed separately from the other steps of the method, and wherein each step of the method is immediately followed by a rinsing step prior to the start of the next step of the method.

3. The method of claim 1, further comprising contacting one or more of the tissue with a physiologically isotonic solution.

4. The method of claim 1, wherein one or more of the solutions further comprises a protease inhibitor, and wherein the protease inhibitor is a serine protease inhibitor, a metalloprotease inhibitor, ethylenediaminetetraacetic acid (EDTA), phenylmethanesulfonyl fluoride or a combination thereof.

5. The method of claim 1, wherein one or more of the solutions further comprises a bioburden reducing agent, and wherein the bioburden reducing agent comprises penicillin, streptomycin, peracetic acid, ethanol, or a combination thereof.

6. The method of claim 1, wherein the hypotonic solution comprises one or more organic or inorganic buffers, one or more antibiotics or antimycotics, an alkaline pH, and wherein the osmolarity of the hypotonic solution is maintained as hyptotonic to cells, and wherein the first surfactant solution comprises a salt selected from the group consisting of KCl and NaCl, one or more organic or inorganic buffers, one or more antibiotics or antimycotics, an alkaline pH, one or more protease inhibitors, and 0.2-3% v/v of a anionic, non-ionic, zwitterionic or cationic detergent selected from the group consisting of Triton X-100, Triton X-200, Tween 20, Tween 80, sodium deoxycholate, CHAPS, N-lauroyl-sarcosinate, Igepal CA630, and Sulfobetain-10 and -16, and wherein the nuclease enzyme solution comprises an endonuclease selected from the group consisting of DNAse, RNAse, and Benzonase, wherein the nuclease enzyme solution is prepared with a physiological buffer selected from the group consisting of Hanks' Balanced Salt Solution, HEPES, Phosphate Buffered Saline, Tris-Buffered Saline, and wherein the nuclease enzyme solution is maintained at a pH of 6-8, and wherein the cleaning solution comprises 0.2-3% v/v of an anionic, non-ionic, zwitterionic or cationic detergent selected from the group consisting of Triton X-100, Triton X-200, Tween 20, Tween 80, sodium deoxycholate, CHAPS, N-lauroyl-sarcosinate, Igepal CA630, and Sulfobetain-10 and -16 or Tri-n-butyl phosphate, one or more organic or inorganic buffers, one or more antibiotics or antimycotics, an alkaline pH, and wherein the cleaning solution is prepared in either an aqueous or a 70% ethanol solvent.

7. The method of claim 1, wherein the first surfactant solution comprises an anionic surfactant, and wherein the anionic surfactant is Triton X-100.

8. The method of claim 1, further comprising carrying out one or more steps at a temperature of between about 22° C. and 40° C.

9. The method of claim 1, wherein the human tissue is a human skin tissue, and wherein the human skin tissue is human allogeneic skin.

10. The method of claim 1, wherein the human tissue is a soft human tissue, and wherein the soft human tissue is a heart valve, tendon, ligament, artery, vein, diaphragm, pericardium, fascia, dura mater, tympanic membrane, aortic conduit, or cartilage.

11. The method of claim 1, wherein the human bioprosthetic tissue is human dermis.

12. The method of claim 1, wherein the cleaning solution further comprises tri-n-butyl phosphate.

13. A bioprosthetic tissue according to the method of claim 1.

14. The method of claim 1, wherein the bioburden reducing agent solution comprises 1% v/v Peracetic Acid in ethanol.

15. The method of claim 1, wherein the cleaning solution comprises 1% v/v TnBP in 70% ethanol solvent.

16. The method of claim 1, wherein in the hypotonic solution the epidermal layer of the human tissue separates from the underlying dermis while leaving the basement membrane intact.

* * * * *